United States Patent [19]

Jacob et al.

[11] Patent Number: 4,912,044
[45] Date of Patent: Mar. 27, 1990

[54] PREPARATION OF MESOPHILIC MICROORGANISMS WHICH CONTAIN A D-HYDANTOINASE WHICH IS ACTIVE AT ELEVATED TEMPERATURE

[75] Inventors: Elard Jacob, Eisenberg; Karsten Henco, Heidelberg; Stefan Marcinowski, Ludwigshafen; Gerhard Schenk, Schwetzingen, all of Fed. Rep. of Germany

[73] Assignee: BASF Aktiengesellschaft, Ludwigshafen, Fed. Rep. of Germany

[21] Appl. No.: 914,791

[22] Filed: Oct. 3, 1986

[30] Foreign Application Priority Data

Oct. 9, 1985 [DE] Fed. Rep. of Germany ....... 3535987

[51] Int. Cl.⁴ .................... C12N 1/22; C12N 9/86; C07H 15/12
[52] U.S. Cl. ...................... 435/172.3; 435/252.33; 435/231; 435/280; 435/849; 536/27; 935/14
[58] Field of Search ............ 435/68, 832, 172.3, 435/253, 849, 231, 252.33, 231, 899, 280; 536/27

[56] References Cited

U.S. PATENT DOCUMENTS 4,493,893 1/1985 Mielenz et al. .................. 435/172.3

FOREIGN PATENT DOCUMENTS 3031151 of 1986 Fed. Rep. of Germany.
53-136583 of 1978 Japan.
54-084086 of 1979 Japan.
55-104890 of 1980 Japan.
60-241888 of 1985 Japan.

OTHER PUBLICATIONS

Andersen et al, J. of Bacteriol., vol. 160, #3, pp. 748–754.
European Search Report for EP 86 11 3833.

Primary Examiner—Thomas G. Wiseman
Assistant Examiner—Patricia A. Carson
Attorney, Agent, or Firm—Oblon, Spivak, McClelland, Maier & Neustadt

[57] ABSTRACT

A description is given of a genertic engineering process for the preparation of mesophilic microorganisms which contain a hydantoinase active at elevated temperature, and of DNA sequences which code for this enzyme.

5 Claims, 15 Drawing Sheets

FIG. 1

AMINO ACID HOMOLOGY

AMINO ACID HOMOLOGY BETWEEN D-HYDANTOINASES FROM CBS 303.80 AND Lu 1220

```
              1                    10                   20                   30
CBS 303.80    P L  L I K N G E  I I T A D S R  Y K A D I Y A E G E T  Y T R I G Q N L
Lu 1220       T K  I I K N G T  I V T A T D T  Y E A D L L I K D G K  I A R I G Q H L
```

53% HOMOLOGY IN THE FIRST 19 AMINO ACIDS

| | |
|---|---|
| 1-50 | CGTTGGAGAA AATATATGGC GCGTTTTCTT CAGGGGAAAC GGCTTTGCAA |
| 51-100 | GTCCCNNAGC GTGCAATCGA CTTCGCTTTG TTGCGAAGGC CGAAGTTTGC |
| 101-150 | CTTGGGTCAG GCTATCGGTA TTTTATACTT GCAGAGTCTG TTAATGGAAG |
| |                                 ├─────── → 3A8 |
| 151-200 | AAACATTTCC ATCGGTACCA CCAACAGACC ATTTACACAA TAGCAAGACC |
| |                  ├─────── → IF10 |
| 201-250 | CAGTTCGGCA AATACGGTGG TTTGTTTTGT TGGACAACCA ACAGGATACG |
| | ├─────── → ID2 |
| 251-300 | CTGTTGTGTA TGATGCCAGA TTCGTTGCTG ATTCCATAAG AAGAAAGTAC |
| 301-350 | GGCTTGTAAA CATAAGGGAG AAACGT[ATG]C CTTTACTGAT CAAGAACGGC |
| 351-400 | GAAATCATCA CCGCGGACAG CCGGTACAAG GCCGACATCT ANGCNGAGGG |
| 401-450 | CGAGACCATC ACCCGCATCG GCAGAACCT CGAGGCCCCG CCCGGCACCG |
| 451-500 | AGGTGATAGC CCACCGGCAA GTACGTGTTT CCCGGCTTCA TAGACCCCCA |
| 501-550 | CGTGCACATC TACCTGCCCT TCATGGCCAC CTTCGCCAAG GACACCCACG |
| 551-600 | AGACCGGCTC CAAGGCGGCC TTGATGGGGG GCACCACCAC CTACATCGAG |
| 601-650 | ATGTGCTGCC CCAGCCGCAA CGACGAGCCC TCGAGGGCTA CCAGCTCTGG |
| 651-700 | AAGAGCAAGC CGAGGGCAAC AGCTACTGCG ATTACACCTT CCACATGGCC |
| 701-750 | GTCCCCAAGT TCGACGAAAA AACCGAGGGG CAGCTGCGGG AGATTGTGCC |
| 751-800 | GACGGCATTA GCTCCTTCAA AATTTTTCTC TCCTACAAAA ACTTCTTTGG |
| 801-850 | CGTGGACGAC GGGGAGATGT ACCAGACCCT GCGCCTAGCC AAGTGAGCTG |

*FIG. 6A*

| | | | | |
|---|---|---|---|---|
| 851-900 | GGGGTGATCG | TGACCGCCCA | CTGTGAGAAN | NNNNNNCGAT AAAACCTACG |
| 901-950 | CCGAGCGGGG | CGGGGTGGAG | GCCATGAAGT | ACATCATGTC GCCGNNCGAT |
| 951-000 | AAGCGCAACC | AGAAAGTCCT | GTGGGGCCCT | GCCCAGGGCT TCATCGACAC |
| 1001-050 | CGTGGGCACC | GACCACTGCC | CCTTCGACAC | CGGCAGAAGC TGCTGGGCAA |
| 1051-100 | GGAGGCCTTC | ACCGCTATTC | CCAACGGCAC | CCGGCCATCG AAGACCGGGT |
| 1101-150 | CAACCTGCTC | TACACCTACG | GGGTGGACCG | CGGCCGCCTC GATATTCACC |
| 1151-200 | GCTTTGTGGN | GGCTCAGCAC | CAAGGCCGCC | AAGTTGTTTG ACTGTTCCC |
| 1201-250 | CCGCNNNNNN | NNNAACAACG | ACTACAACGG | CTTCGAGGGC TTTGAGATTG |
| 1251-300 | ACGGCCGGCC | CAGCGTGGTG | ACGGTGCGGG | GTAAGGTGGC GGTGCGGGAC |
| 1301-350 | GGGCAGTTTG | TGGGCGAGAA | GGGGTGGGGT | AAGCTCCTGC GGCGCGAGCA |
| 1351-400 | TGTACTTCTA | AATGAAGCCG | AGATGGGTTT | TGNATTTGCT GGGTGGGATC |
| 1401-450 | TGCCTGTGGA | TAGCGGTGGT | GCTGGTGCTG | GGGGTAGTT CGGCCTGGGC |
| 1451-500 | GCTTTTTGCG | GTAGTCGGCG | AACTCCTGTT | GGTGCTGGCC CAAAGAGGCT |
| 1501-550 | TCAAGCGGAG | ATAGATGGTA | GGTGAATAAT | CCTGACGGGC AGCCGCCATA |
| 1551-600 | AATAGGGAAG | ACCATGATGC | AAGCCAATAC | CTCTCCAGAG CTGTCCGCCA |
| 1601-650 | AAGGTTCGAA | CGCAGCCGCC | GTTCGGTTC | AGGGTGTTTC GATGGTGTTT |
| 1651-700 | CCCAACGGAA | CCGTGGCCCT | CAAAGACGCC | AACCTCGAGA TCGCCNAGGG |
| 1701-701 | G | | | |

FIG. 6B

| | |
|---|---|
| 1-050 | CGGTTATGGA TATTGTTGGG AAGTCAGTTC ATAAATATTC CAATTGGGGG |
| 51-100 | GACCTCGACC TTCATTATAA AGTGGTTGTT CGCATTAACA AAGATGTTTG |
| 101-150 | CATTAATTGC AATAAATGTT ATATCTCCTG TGAAGATGCT TCTCATCAAT |
| 151-200 | GCATTGATCG TTTAACGGAT GAAAATGGAA AAGAGTATTT AAAAGTGCGC |
| 201-250 | GAAGAAGATT GCGTAGGGTG TAATTTATGT TCGATCGTCT GTCCGGTGGA |
| 251-300 | TGGTGCGATT GACATGGTCG AAATGCCAAG CGACAATCTG CCGATGACAT |
| 301-350 | GGAATGAACG CCAAGCGGCC ATTAGCGGGC TGAGCAGCTG TAGCGTTGAT |
| 351-400 | GTGAAATAAA ACGAAATTTC CAGCGGAGGA GGATGTTGAA ATGACAAAAA |
| 401-450 | TAATAAAAAA TGGAACGATT GTTACCGCAA CCGATACGTA TGAAGCGGAC |
| 451-500 | TTGCTCATTA AAGACGGAAA AATTGCCATG ATAGGCCAAC ATTTAGAAGA |
| 501-550 | AAAAGGCGCT GAAGTGATTG ATGCCAAAGG CTGTTACGTA TTTCCAGGCG |
| 551-600 | GTATTGATTC GCACACGCAT TTAGATATGC CGTTTGGCGG CACGGTGACA |
| 601-650 | AAGGATGATT TCGAATCTGG AACGATTGCG GCGGCATTTG GCGGAACAAC |
| 651-700 | GACCATCATC GACTTTTGTT TAACGAATAA AGGGGAGCCA TTAAAAAAAG |
| 701-750 | CGATTGAAAC TTGGCACAAC AAAGCGAAGG GAAAAGCGGT TATTGATTAT |
| 751-800 | GGCTTCCATT TAATGATTAG CGAAATTACG GATGACGTAT TAGAAGAGCT |
| 801-850 | GCCAAAAGTC ATTGCCGAAG AAGGGATAAC ATCCTTTAAA GTGTTTATGG |
| 851-900 | CGTATAAAAA CGTATTTCAG GCAGATGATG GAACGTTATA CCGCACGCTA |
| 901-950 | GTGGCTGCCA AAGAACTTGG CGCGCTTGTC ATGGTTCATG CGGAAAATGG |

Near line 351-400: ⊢——p70  ⊢—p62 (above ATG box)
Near line 401-450: ⊢—p51

*FIG. 12A*

951-000 GGATGTGATT GATTACTTAA CGAAAAAAGC GCTTGCGGAA GGGAATACGG 1001-050 AGCCGATTTA CCATGCTTTA ACGCGGCCTC CAGAAGTAGA AGGAGAAGCG 1051-100 ACCGGGCGCG CCTGTCAATT GACAGAGCTT GCCGGTTCAC AACTTTACGT 1101-150 TGTTCACGTG ACATGTGCGC AAGCGGTGGA AAAAATTGCA CAAGCGCGCA 1151-200 ATAAAGGGTT GGATGTGTGG GGAGAAACGT GTCCGCAATA TCTTGTTCTC 1201-250 GACCAATCGT ATTTAGAAAA GCCTGATTTT GAAGGCGCGA AATATGTTTG 1251-300 GTCCCCTCCG CTTCGTGAAA AATGGCATCA AGAAGTATTG TGGAATGCGC 1301-350 TGAAAAACGG CCAGCTGCAA ACGCTTGGAT CGGACCAATG TTCATTTGAC 1351-400 TTTAAAGGCC AAAAAGAACT TGGCAGAGGA GATTTACTA AAATTCCAAA 1401-450 CGGCGGGCCG ATGGTCGAGG ATCGGGTCAG CATTCTTTTC AGTGAAGGGG 1451-500 TTAAAAAAGG AAGAATCACG TTAAATCAAT TTGTCGATAT TATGTCGACA 1501-550 AGAATTGCCA AATTGTTCGG GTTATTCCCG AGAAAAGGAA CGATCGCGGT 1551-600 AGGTTCAGAC GCAGACTTAG TCATTTTTGA CCCGGATATC GAACGGGTGA 1601-650 TTTCGGCGGA ACACACCAT ATGGCCGTCG ACTATAATGC ATTTGAAGGA 1651-700 ATGAAAGTAA CGGGTGAACC GGTATCGGTT CGTGCAGAGG CGAATTTGTT 1701-750 GTCCGTGATA AACAATTTGT CGGAAAACCA GGGTACGGCC AATATTTAAA 1751-800 ACGGGCAAAA TACGGAACCT CAAAGATTTC CAAGCAGAAC GAGAAATTAA 1801-850 CCATTTAAAA GAATAACAAC CTACTCTTGC CCCTTAAAAT GCCAATAAAA 1851-900 TGCAACACTT AGCTTTATTC CCGTTCTAAG CAG

*FIG. 12B*

PREPARATION OF MESOPHILIC MICROORGANISMS WHICH CONTAIN A D-HYDANTOINASE WHICH IS ACTIVE AT ELEVATED TEMPERATURE

Dihydropyrimidinases [EC 3.5.2.2] catalyze the cleavage of racemic hydantoins into the corresponding D-N- and L-N-carbamoyl-alpha-amino acids. D-N-Carbamoyl-alpha-amino acids are important intermediates for the preparation of D-amino acids which are used as valuable starting materials for the production of semi-synthetic penicillins and cephalosporins.

A dihydropyrimidinase from a thermophilic microorganism has been described (I), which enzyme is able to cleave D,L-hydantoins stereoselectively into D,N-carbamoyl-alpha-amino acids, there then being, owing to the high transformation temperature at which the enzyme is active (40° to 90° C.), spontaneous racemization of the uncleaved L-hydantoin. This dihydropyrimidinase, which may also be called D-hydantoinase owing to its specificity for hydantoins, can be obtained by fermentation of asporogenic, Gram-negative thermophilic microorganisms or thermophilic Bacillaceae and can be used as a crude detergent lysate, where appropriate after immobilization, for the cleavage of D,L-hydantoins. However, the thermophilic microorganisms which are used grow to only a low cell density. Furthermore, the content of D-hydantoinase constitutes only a few parts per thousand of the total microorganism protein.

In principle, it is possible to increase the fermentation yield in two ways:

1. Attempts can be made to modify the microorganisms, by mutagenesis using chemical or physical methods, in such a way that they provide a significantly higher yield of enzyme. However, the search for substantially improved microorganisms involves much effort and its result is uncertain.

2. Attempts can be made to isolate the gene which is responsible for enzyme production from a microorganism, and to modify it in such a way that, after implantation in the original donor organisms or another microorganism which can act as recipient for this gene and can transmit it to subsequent generations in a stable manner and maintain its ability to function, it results in increased enzyme production.

It is also possible to carry out specific modifications in the region of the DNA sequences associated with the gene or in the region of the gene itself in order to increase the activity of enzyme production and to stabilize the enzyme.

Finally, the enzyme production of the cells can also be raised by increasing the number of identical genes responsible for enzyme production in each cell.

Although many transplantations of genes have already been carried out successfully (II–VI), it is impossible in specific cases to predict whether transplantation of a gene will lead to a successful result.

The present invention relates to a process for the preparation of mesophilic microorganisms which contain a D-hydantoinase which is active at elevated temperature, which process comprises (a) isolation and fragmentation of the DNA from a thermophilic microorganism which cleaves D-hydantoin, (b) combination of the resulting DNA fragments with a cloning vector, (c) integration of the resulting recombinant cloning vectors into a mesophilic microorganism and (d) selection of those microorganisms which express enzymatically active D-hydantoinase.

The present invention further relates to DNA sequences coding for D-hydantoinase and obtainable from thermophilic microorganisms and to cloning vectors which contain these sequences, as well as to mesophilic microorganisms containing these cloning vectors, and to the use thereof for the preparations of thermophilic D-hydantoinases and for the cleavage of D,L-hydantoins.

The preparations of the mesophilic microorganisms which cleave D-hydantoins and are obtainable by gene manipulation starts from thermophilic microorganisms which cleave D-hydantoins. Examples of microorganisms of this type are Thermus spec. and the thermophilic representatives of the Bacillaceae family. They can be obtained by brief heating to about 100° C. of soil-containing or wet samples from nutrient-rich wet biotopes, incubation in nutrient medium at about 60° C., and selection for D-hydantoinase activity (I). Two strains of this type have been deposited (CBS 303.80 and CBS 363.80).

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 illustrates the amino acid homology between the D-hydantoinases from CBS 303.80 and Lu1220;

FIGS. 6a and b illustrate the nucleotide sequence for a DNA fragment from CBS 303.80 which contains a D-hydantoinase gene;

FIGS. 12a and b illustrate a nucleotide sequence for a DNA fragment from Lu1220 which contains a D-hydantoinase gene;

DETAILED DESCRIPTION OF THE PREFERRED EMBODIMENTS

Figure 2:
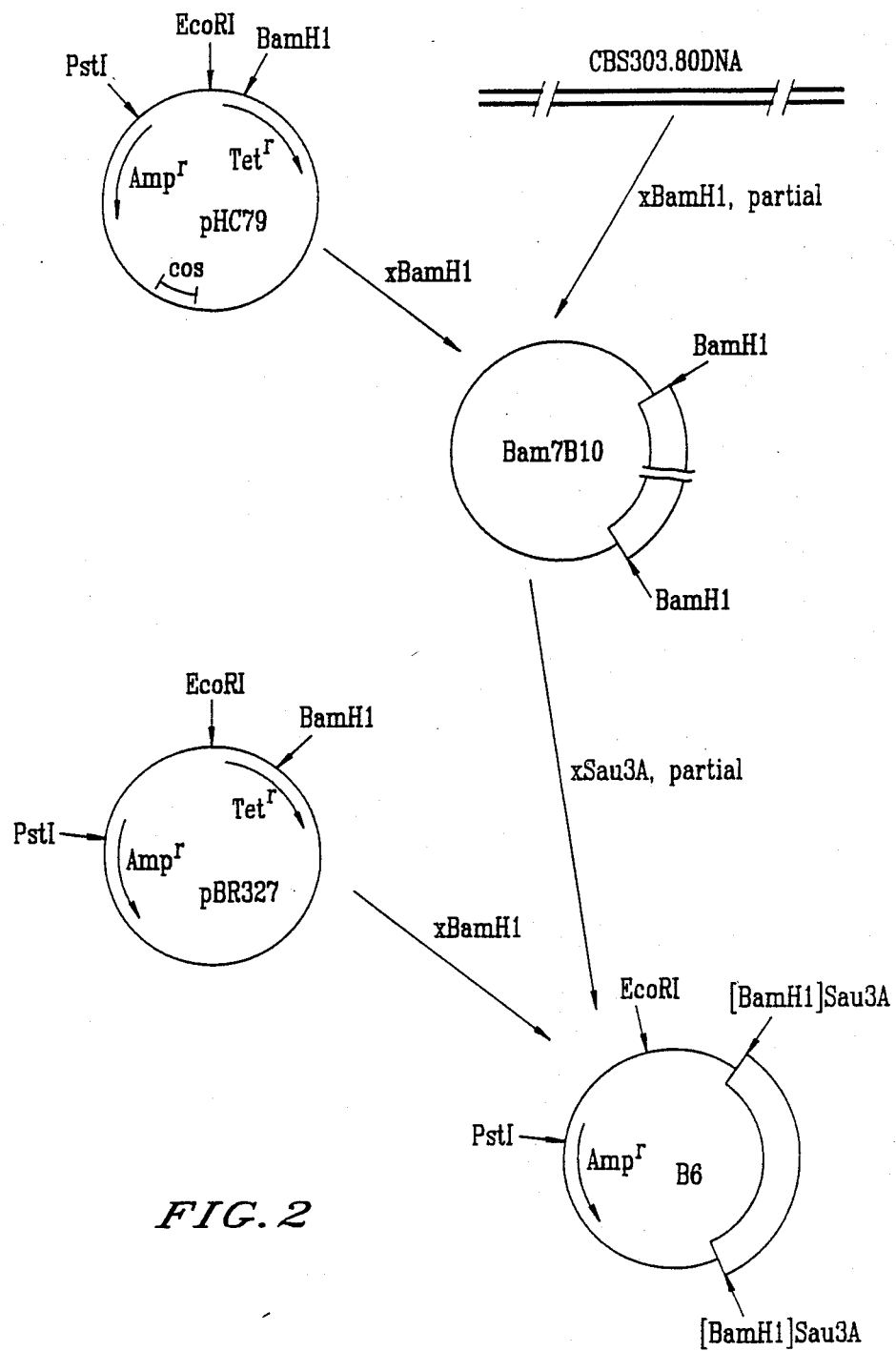
FIG. 2 illustrates a sequence of steps for preparing the plasmid B6.

The DNA from these microorganisms, called the donor DNA, is isolated by destroying their cell walls, for example with an enzyme such as lysozyme and/or a detergent, precipitating the major amount of protein from the resulting lysate using phenol-containing solutions, and subsequently removing residual protein by enzymatic cleavage and subsequent dialysis. The donor DNA can be obtained pure from the resulting solution by equilibrium gradient centrifugation and subsequent dialysis.

It is necessary for the isolation or enrichment of the D-hydantoinase gene to fragment the donor DNA. This can be effected physically by the action of shear forces or chemically by enzymatic cleavage.

Physical fragmentation is effected by, for example, ultrasonic treatment, high-speed agitation in a homogenizer, forcing through narrow-lumen cannulas or repeated freezing and thawing of the DNA (VII).

The enzymatic fragmentation of the donor DNA can be carried out using, for example, randomly cleaving DNases under conditions at which double-strand breaks preferentially occur (VIII).

It is then necessary to convert the fragmented donor DNA, by attachment of linker or adaptor sequences, into a form in which it can be integrated into a vector DNA. The donor and vector DNA can also be connected together by extending both with mutually complementary bases and coupling them together.

It has proved particularly useful to cleave the donor DNA with a restriction endonuclease which exposes at the ends of the DNA fragments defined nucleotide sequences which depend only on the nature of the restriction endonuclease. When plasmids pBR322 or pBR327 (IX-X), or plasmids derived therefrom, such as pHC79 (XI), are used as vector DNA, particularly suitable restriction endonucleases are EndoR.BamHI, EndoR.HindIII, EndoR.EcoRI or EndoR.PstI. [The name of the enzymes is usually abbreviated by omission of the name of the type (EndoR)]. These cut the said plasmids only once and result in a linear vector DNA into which the donor DNA fragments can be integrated in a manner which is especially readily controllable. Combinations of certain restriction endonucleases which liberate homologous terminal sequences of the cleaved DNA are also suitable; for example the donor DNA can be fragmented with EndoR.Sau3A which cuts at many recognition sites. It is then possible to integrate the fragments, by the action of DNA ligase [E.C. 6.5.1.1], into vector DNA which has been cut with EndoR.BamHI. If the fragmentation of the donor DNA is carried out with a low concentration of a restriction endonuclease of this type, which cuts at many points, it is possible to obtain virtually randomly generated DNA fragments, and the size of the fragments depends on the enzyme concentration and the time for which it acts. It is also possible in this way to clone DNA fragments which, by reason of their specific base sequence, possess no recognition sites, or possess recognition sites which are not sufficiently close to the gene which is sought, for the less frequently cleaving restriction endonucleases such as those listed above.

The fragments of the donor DNA are incorporated in the linearized vector DNA. This can be effected with DNA ligases which can be obtained from E. coli cells which have been infected where appropriate with T4. A cofactor (NAD+ or ATP) is required for the incorporation.

Suitable vector DNA is DNA from plasmids, cosmids or bacteriophages. It is advisable to use linearized cosmids or the DNA of bacteriophage λ for the initial incorporation steps, and to use plasmids for the subsequent incorporation steps, because cosmids or bacteriophage λ DNA allow the cloning of much larger DNA fragments than does plasmid DNA. Typical maximum sizes for DNA fragments which can be cloned in a cosmid or bacteriophage vector are from about 50 to 23 kb (1 kb corresponds to 1,000 basepairs of double-stranded DNA). This means that the number of independent clones which must be tested for the expression of D-hydantoinase is kept low. For example, when a fragment 40 kb in size is integrated into a cosmid vector, the entire DNA of one microorganism is, with a probability of 99%, obtained in about 350 independent clones, whereas with a fragment 6 kb in size, which is in the typical size range for a plasmid cloning, the number of clones to be examined increases to about 2,300.

However, after the coding DNA sequence which is sought has been found, the adjacent undesired DNA sequences, which have initially and unavoidably also been cloned, must be removed in order to achieve the highest possible stability. Most suitable for this purpose is incorporation into plasmids, especially since the, frequently necessary, manipulation of the DNA in the form of restriction enzyme digestion and ligation is facilitated by the reduced size of the DNA.

The resulting hybrid vector is introduced into a suitable host cell. Examples are E. coli cells with defined genetic markers, in particular those which have a defect in the restriction/modification system ($r^-m^-$), are recombination deficient ($recA^-$) and have, where appropriate, a thermolabile lambda repressor (cI857).

Particularly suitable and preferred host cells are E. coli HB 101, NF1, W6(λrex) and N4830.

Detection of whether gene cloning has succeeded depends crucially in this stage on whether a specific detection reagent for the gene is available. In general, this can be a nucleic acid or a fragment thereof which is isolated from the donor cell or a segment, which has already been cloned previously, of the relevant gene or a sequence adjacent thereto or which has been synthesized chemically by use of a partial amino acid sequence of the protein product for which the particular gene codes. Finally, it is also possible to utilize the capacity of the gene to produce, in the foreign recipient cell, the protein product which it specifies, it being necessary in this case for an antibody to detect the protein products to be available or it being possible to detect the protein product via its enzymatic activity where appropriate. In both cases, it is necessary for the gene (A) which is sought also to have signal sequences which can function in the recipient cell as promoter and terminator of transcription and ribosome binding site (for the definition of these terms see XII). With this in view, as well as owing to the effort involved in screening by an enzymatic assay, it is advantageous to carry out the initial clonings with large DNA fragments, for which cloning in a cosmid or phage vector is appropriate.

In order further to improve the expression of the resulting gene (A), it is also possible for the said signal sequences to be provided by another gene (B). Examples of other genes (B) are the DNA equivalent of a segment of MS2 replicase (XXVI) and the cro gene fragment of bacteriophage λ (XXXVI).

However, it is initially advantageous to introduce the gene from the cosmid into a small plasmid. For this purpose, the cosmid DNA which contains, inter alia, the gene (A) is isolated and cut in several batches with a DNase for different lengths of time. The batches are combined and fractionated according to size by electrophoresis or chromatography. The DNA fraction in the molecular weight range which corresponds to the size of the intact gene is isolated and purified. The resulting DNA is ligated with linearized plasmid DNA which has at least one resistance marker. The ligation mixture is transformed into bacterial cells. The resulting cells are cloned in a medium which contains the substance against which the plasmid which is used confers resistance on the host cell. The hydantoinase-producing clones are isolated.

A clone of this type is used for further optimization of expression. For this purpose, initially the plasmid contained therein is isolated and linearized in a known manner. The resulting linear DNA is digested with a DNase which acts progressively from the ends of the molecule, and finally, after attachment of DNA linkers, is cyclized again. The linearization at the start of this process is carried out with those restriction enzymes which permit, in the second step, elimination of undesired DNA sequences upstream and downstream of the gene by the progressively acting DNase.

The plasmids which have been recircularized by the ligation are then transferred into a bacterium and cloned. The D-hydantoinase-expressing clones are selected in such a way that they contain as little as possible of original DNA outside the D-hydantoinase coding sequence. It is advisable for this purpose to combine a clone which contains as little as possible of original DNA between the 5′-end and an enzyme cleavage site with one which contains as little as possible of original DNA between the 3′-end and an enzyme cleavage site. The combination product is propagated and isolated in a customary manner, and the D-hydantoinase gene is cut out enzymatically. The latter is integrated into a suitable plasmid which possesses a strong promoter and a highly active ribosome binding site, e.g. pPCLC24 derivatives (XXVI) pEX31 or the plasmid pCL 547 (XXXVI).

The resulting plasmids are then transferred into a bacterium. Since the promoters of the said plasmids are controlled by the lambda repressor $c_I$, the E. coli strains used for the transformation should possess a mutated $c_I$ gene which leads to a temperature-labile repressor. It is possible in such cells to induce the promoters by raising the temperature. The plasmid-containing bacteria are finally selected for D-hydantoinase enzyme activity.

The cloning of the genes was demonstrated via the D-hydantoinase protein products by use of specific polyclonal antibodies, as well as via their enzymatic activity.

Surprisingly, expression of the D-hydantoinase genes isolated from thermophilic microorganisms takes place in the mesophilic E. coli recipient cells without the necessity to provide foreign signal sequences for this purpose. However, the cloned DNA sequence of strain CBS 303.80 proved to be unstable in various stages of construction after partial deletion of the co-cloned DNA sequences 3′-proximal to the gene, and it had to be selected from the resultant mutants by thorough restriction and sequence analysis. The gene was stable again, however, with a residual length of the 3′-sequences of 25 to 125 nucleotides downstream of the translation stop signal of the D-hydantoinase gene of CBS 303.80 and about 250 nucleotides upstream of the start signal (5′-proximal to the gene). Although, finally, on optimization of expression for the two D-hydantoinase genes, an attempt was made to couple to another gene (MS2 replicase fragment in the pEX constructs, cro gene fragment in the pCL constructs (see Examples 1.8 and 2.6)), in fact a fusion protein was detectable in only one case. This fusion protein likewise had D-hydantoinase activity. In all other cases D-hydantoinases of natural length were found. Surprisingly, the synthesis of the enzymes was (temperature-) inducible in these constructs. It resulted in an enzyme activity (based on cell mass) which was 4 to 40 times that in the initial strains (40 times higher for CBS 303.80).

The Examples detailed below describe the successful cloning of two unrelated, D-hydantoinase genes, which exhibit a limited homology (52%) only in the first 19 amino acids of the amino terminal end (FIG. 1; boxes have been placed round the positions where the amino acids are identical).

EXAMPLE 1

1.1 Isolation of the DNA 200 ml of Castenholz nutrient medium (XIII) (= 10 ml of basal medium [889 ml of $H_2O$, 33.4 mg of $FeCl_3 \times 6H_2O$, 20.48 mg of $MgSO_4 \times 7H_2O$, 0.8 g of NaCl, 10.3 g of $KNO_3$, 68.9 g of $NaNO_3$, 10 g of Titriplex III, 7.59 g of $CaSO_4 \times 2H_2O$, 100 ml of trace element solution [containing per liter 0.5 ml of concentrated $H_2SO_4$, 2.69 g of $MnCl_2 \times 4H_2O$, 0.72 g of $ZnSO_4 \times 7H_2O$, 0.5 g of $H_3BO_3$, 78 mg of CuCl, 28.75 mg of $Na_2MoO_4 \times 2H_2O$, 94.94 mg of $CoSO_4 \times 7H_2O$], 2.5 g of yeast extract, 2.5 g of bactotryptone, 0.258 g of $Na_3PO_4 \times 12H_2O$ per l) were inoculated with 10 ml of cells of the asporogenic Gram-negative thermophilic bacterial strain CBS 303.80 from a fresh overnight culture and shaken at 60° C. for 24 h. The bacterial culture was centrifuged at 4,000 to 8,000 × g for 20 min, and the sediment was resuspended in 200 ml of solution A (50 mM Tris-HCl, pH 8, 10% sucrose), again centrifuged, and resuspended in 16 ml of solution A. While mixing, 3.2 ml of a hen's egg-white lysozyme solution (5 mg/ml in solution A) were added. After incubation at room temperature for 15 min, 4 ml of 0.5M EDTA solution, pH 8.0, were added, the solution was mixed by shaking and, after a further 5 min at room temperature, 20 ml of solution B (50 mM tris-HCl, pH 8, 10 mM EDTA, 0.5% Triton X100) were pipetted in with rapid mixing. Immediately thereafter 2.6 ml of 10% strength sodium dodecyl sulfate solution were added. After mixing, the highly viscous cell digest was maintained at 60° C. for 10 min. After addition of 5 ml of 5M sodium perchlorate solution, the cell lysate was shaken with 50 ml of phenol/chloroform/isoamyl alcohol [25 parts by volume of phenol (equilibrated with 0.1M tris-HCl, pH 7.4, 0.05M NaCl, 10 mM EDTA and 0.01% β-hydroxyquinoline), 24 parts by volume of chloroform, 1 part by volume of isoamyl alcohol] at 40° C. for 30 min. The emulsion was separated by centrifugation at 4,000 × g for 10 min. The isolated upper phase was extracted twice with phenol/chloroform/isoamyl alcohol as described above and then with the same volume of chloroform. The upper aqueous phase was dialyzed against 4 l of 50 mM tris-HCl, 50 mM NaCl, 5 mM EDTA, pH 8, at 4° C. for 16 h, adjusted to a salt concentration of 0.15M NaCl, 50 mM tris-HCl, 5 mM EDTA, pH 8, and incubated with DNase-free RNase (final concentration 0.1 mg/ml) at 37° C. for 30 min. This mixture was extracted as described above once with phenol/ chloroform/isoamyl alcohol and twice with chloroform.

5 ml of the resulting aqueous solution (DNA content 30 μg/ml) were adjusted to a final concentration of 10 mM with sodium tetraborate and to a refractive index of 1.400 with solid cesium chloride (about 1.36 g/ml of DNA solution). After ultracentrifugation at 140,000 × g (48 h, 20° C.) the contents of the centrifuge tube were fractionated by dropwise removal after the base of the tube had been punctured. The DNA-containing fractions were identified by measurement of UV absorption (260 nm) and were dialyzed against 4 l of solution C (2 mM tris-HCl, 2 mM NaCl, 0.1 mM EDTA, pH 8) at 4° C. for 16 h.

1.2 Shotgun cloning in the cosmid vector pHC79

20 μg samples of the DNA obtained as in 1.1 were dissolved in 0.2 ml of 100 mM tris-HCl, pH 7.5, 50 mM NaCl, 10 mM $MgCl_2$, and were cleaved with 2.0 U of BamHI for 10, 20 and 30 min respectively. The reaction mixtures were combined and deproteinized by phenol treatment, and the DNA was concentrated by ethanol precipitation at −70° C. for 10 min after addition of 2.5 parts by volume of ethanol (salt concentration: 0.3M sodium acetate, pH 5). The cosmid pHC79 (XI; FIG. 2) was linearized by digestion with 1.5 U of BamHI/μg DNA in 100 mM tris-HCl, pH 7.5, 50 mM NaCl, 10 mM $MgCl_2$ and 6 mM DTT, deproteinized and concentrated by ethanol precipitation. 7 μg of the DNA from CBS 303.80 which had been partially cleaved with BamHI, and 0.1 μg of the BamHI-cleaved DNA of the cosmid pHC79 were ligated with 0.1 U of T4 DNA ligase in 20 mM tris-HCl, pH 7.5, 10 mM $MgCl_2$, 10 mM DTT, 0.6 mM ATP and 100 μg/ml bovine serum albumin, at a DNA concentration of 800 μg/ml, at 12° C. for 2 h. The ligation mixture was packaged in vitro into lambda phage particles (XIV) and used for infection of E. coli HB 101 (XV). The infected cells were streaked onto LB/Amp agar (L broth: 1% Bacto tryptone, 0.5% Difco yeast extract, 0.5% NaCl, 10 μg/ml thiamine, 1% Difco agar, 100 μg/ml ampicillin).

1.3 Preparation of an antibody against D-hydantoinase

(i) Preparation of pure D-hydantoinase 500 g of dry biomass of the strain CBS 303.80 which cleaves D-hydantoins were suspended in 5,000 ml of distilled water and, while cooling in ice, disrupted in a glass bead mill (bead size 0.35 to 0.4 mm) at a pumping rate of 200 ml/min. Then 20% strength aqueous polymin P solution was added to a final concentration of 0.4%. After centrifugation at 3,000 × g for 15 min, the supernatant was diluted with distilled water until the conductivity was 2 mSi, and was stirred with 230 g of Whatman DE-52 cellulose ion exchanger (22° C., 90 min). The bound enzyme was eluted with 0.1M borax-HCl, 0.2M NaCl, pH 8.5, and after removal of salt was fractionated on a DEAE A-50 Sephadex column with a gradient from 0.1 to 0.2M NaCl in 50 mM borax-HCl, pH 8.5. After dialysis of the eluate against 20 mM borax-HCl, pH 8.5, salts were removed from the enzyme preparation on an AcA44 Ultrogel column (LKB) and, after adjustment to 0.5M in ammonium sulfate, it was further fractionated by hydrophobic chromatography on Octylsepharose CL4B (Pharmacia). The main peak was pure according to analysis by isoelectric focussing and SDS-polyacrylamide gel electrophoresis. The yield was 10%.

The resulting D-hydantoinase solution was dialyzed against 0.1M borax-HCl and 0.1M sodium citrate, pH 8.5, and placed on a crystallization dish. The solution was concentrated in a closed chamber over a 0.5M sodium citrate solution, pH 7.0, which was replaced after 4 days by a 0.8M sodium citrate solution, pH 7.0. After 8 days large protein crystals with D-hydantoinase activity had been produced.

The amino acid sequence of the amino terminal end, of internal tryptic peptides and of the carboxyl terminal end of the D-hydantoinase obtained from the strain CBS 303.80 was determined by automatic sequencing via Edman degradation (XVI). The following partial sequences were found for the protein (XVII).
PLLIKNGEIITADSRYKADIYAEGXTIT(-R)I(GQNLEAP) N-terminal end
TGPEWHEPS(RPXAV)
KGTIAVGSDADLVVY
TQHVNNDYNGFEGF
$NFF_L{}^G$.

(ii) Obtaining the antibody

Three rabbits were each injected with 500 μg of a 0.9% strength NaCl solution of the enzyme preparation, obtained as in (i), in complete Freund's adjuvant (Difco), and received subsequent inoculations with half the amount of enzyme after 6 and 10 weeks. 100 μl of the antiserum obtained after week 10 bound 120 μg of D-hydantoinase. The IgG fraction of the rabbit antiserum was obtained by chromatography on protein A-Sepharose.

1.4 Identification of cell clones producing D-hydantoinase

E. coli colonies which produce a particular antigen (sensitivity ~1 pg (XVIII)) can be identified immunologically. The individual steps of this analysis comprise preimpregnation of PVC sheets with an antibody against D-hydantoinase, saturation of all the remaining free binding sites by preimmune serum, formation of an imprint by contact with the lyzed colonies, and binding of radio-labeled antibody against D-hydantoinase. The radioactive antibody binds only where D-hydantoinase, or part sequences thereof, had previously been adsorbed onto the sheet. Autoradiography of the sheet with X-ray film was used to identify the clones (colonies) which synthesize D-hydantoinase or part sequences of the enzyme:

The clones (about 2,000) obtained as in 1.2 were transferred with toothpicks from the agar plate into the wells of microtiter plates, shaken at 37° C. for 16 h, and transferred in the pattern of the microtiter plates to nitrocellulose filters (BA85, Schleicher and Schull) on LB/Amp plates. The colonies, which were about 2 mm in size, were infected with 2.5 to $5 \times 10^5$ lambda vir nin5 pnages (XIX) in 10 mM $MgSO_4$ per colony, and were incubated at 37° C. for 4 h. Subsequently, to complete cell lysis, the plates were exposed to a saturated chloroform atmosphere for 10 min. Then a PVC sheet which had been treated with the IgG fraction of CBS 303.80 D-hydantoinase antibody was laid, free of air bubbles, on the lyzed colonies and incubated at 4° C. overnight. The sheets were impregnated with 60 μg/ml IgG in 0.2M $NaHCO_3$, pH 9.2 (20° C., 2 min) and washed 2 × with 10 ml of cold washing buffer (PBS buffer, 0.5% normal rabbit serum, v/v, 0.1% bovine serum albumin, w/v). The sheets were lifted off, cell residues were carefully removed and incubated in 2.5 ml of washing buffer and $8 \times 10^6$ cpm of $^{125}$I-labeled anti-D-hydantoinase CBS 303.80 IgG at 4° C. for 12 h. The labeling of the IgG fraction of the antibody against CBS 303.80 D-hydantoinase (anti-D-hydantoinase CB 303.80 IgG)

was effected using chloramine T: 20 μl of IgG in 50 mM Na phosphate, pH 7.5, and 5 μl of Na$^{125}$I (Amersham-Buchler, 100 mCi/ml, 13-17 mCi/ μg) were incubated with 10 μl of chloramine T (5 mg/ml in 50 mM Na phosphate, pH 7.5) for 20 sec, and then 10 μl of Na$_2$S$_2$O$_5$ (12 mg/ml in 50 mM Na phosphate, pH 7.5), 100 μl of KI (10 mg/ml) and 1% bovine serum albumin were added, and salts were removed on Sephadex G50 (Pharmacia). The filters were, after incubation, rotated in 100 ml of washing buffer for 2×5 min at 4° C. and in H$_2$O for 2×5 min at 45° C. The dried sheets were exposed with intensifyscreen and Kodak XAR5 X-ray film at −70° C. overnight.

1.5 Detection of the D-hydantoin produced by the clones

The cell clones which had been identified as positive in the immunoassay described above (Broome-Gilbert XVIII) were tested for expression of enzymatically active D-hydantoinase. For this purpose, 50 ml cultures were shaken in L broth which contained 100 μg/ml ampicillin at 37° C. for 16 to 24 h and then centrifuged at 4,000 to 6,000 × g for 10 min. The precipitate was resuspended in 50 ml of solution A, centrifuged, and the sediment was taken up in 130 ml of solution A and incubated with 20 μl of hen's egg-white lysozyme solution (10 mg/ml in 25 mM tris-HCl, pH 8) at room temperature for 20 min. 330 μl of 0.25M EDTA solution, pH 8, were added. After 5 min, 1.67 ml of solution B were added with rapid mixing. The clear lysate was centrifuged at high speed at 4° C. for 1 h, and the supernatant was heated at 70° C. for 2 min, and the precipitate was removed at 4,000 × g and 4° C. for 10 min. 0.5 ml of 0.4M borax-HCl, pH 8.5, 0.1 ml of 1M MgCl$_2$ and 0.625 ml of 5% strength methylthioethylhydantoin solution in 0.1M borax-HCl, pH 8.5, were added to 2 ml of the supernatant. After shaking at 60° C. for 30 min (to convert D,L-methylthioethylhydantoin into N-carbamoyl-D-methionine) 1.5 ml were removed and centrifuged at 8,000 × g for 5 min, and 0.168 ml of 1/10 concentrated phosphoric acid was added to 1.2 ml of the supernatant. The precipitate which formed was centrifuged at 8,000 × g for 1 min, and the supernatant was filtered to remove particles and analyzed for the N-carbamoylmethionine content by HPLC. The spontaneous conversion of D,L-methylthioethylhydantoin into N-carbamoyl-D-methionine under these conditions was determined in the presence of an equal quantity of protein extract from E. coli HB101 (pHC79). Clones whose lysates showed not less than twice the conversion of D,L-methylthioethylhydantoin into N-carbamoyl-D-methionine were assessed as positive.

1.6 Subcloning of the D-hydantoinase gene

The recombinant plasmid DNA of one of the clones producing D-hydantoinase (Bam7B10; for construction see FIG. 2) was isolated by a conventional method (XX). 2 μg samples of plasmid DNA were cleaved at a concentration of 120 μg/ml with 0.5 U of Sau3A per μg of DNA for 10, 20 and 30 min respectively. The reaction mixtures were combined and fractionated by electrophoresis on a 0.8% soft agarose gel in a 50 mM tris-acetate buffer, pH 7.8, which contained 2 mM EDTA and 0.5 μg/ml ethidium bromide. The gel segment which contained DNA in the size range from 2 to 4 kilobases was identified using a UV lamp by comparison with a DNA size standard and was removed and melted at 65° C. with the same volume of solution D (0.1M tris-HCl, 10 mM EDTA, 0.2M NaCl, pH 7.4) for 5 min. After emulsion with the same volume of aqueous phenol at 37° C. (equilibrated with solution D/water=1:1) and centrifugation, the resulting upper phase was extracted twice with chloroform and concentrated by an ethanol precipitation. 1 μg of plasmid pBR327 (x) was linearized with 1.5 U/μg DNA BamHI for 90 min and dephosphorylated with calf intestine phosphatase (CIP) (XXI). 0.5 μg of the plasmid DNA which had been deproteinized by phenol extraction was ligated with 1 μg of the 2-4 kb fraction of Bam7B10 (XXII). CaCl$_2$-treated (XXIII) E. coli HB101 cells (XV) were transformed with the ligation mixture. After growth in antibiotic-free nutrient medium (L broth: 1% Bacto tryptone, 0.5% Difco yeast extract, 0.5% NaCl, 10 μg/ml thiamine) for 90 min, the cells were plated out on LB/Amp plates. The clones which were obtained were tested for those positive for D-hydantoinase as described above in the Broome-Gilbert assay and by detection of production of hydantoin. 3 clones produced enzymatically active D-hydantoinase. One of them, B6 (see FIG. 2) was, after sequencing, used for optimization of expression.

1.7 Sequencing of the CBS 303.80 D-hydantoinase gene in the vector B6

Figure 3:
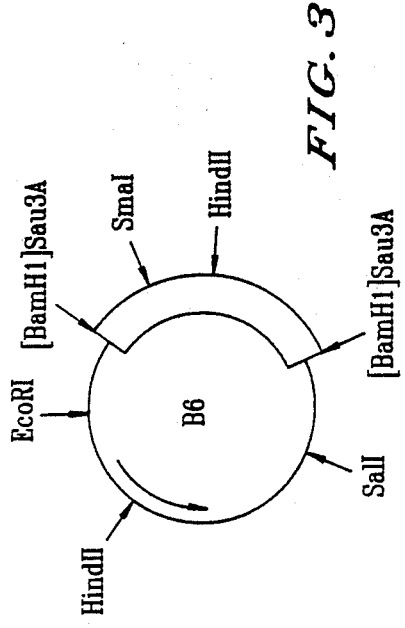
FIG. 3 schematically illustrates the structure of the plasmid B6.
Figure 4:
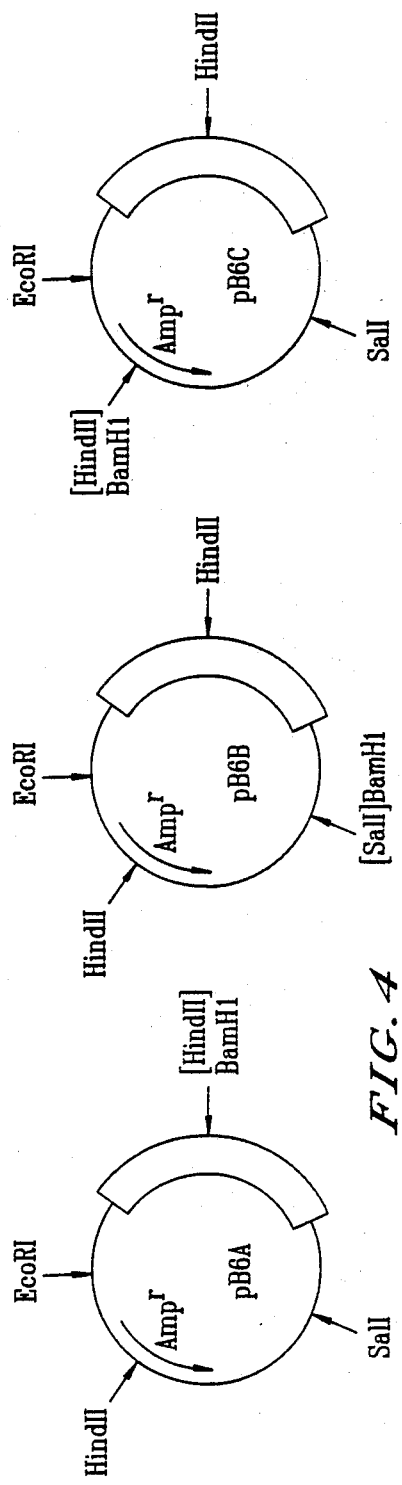
FIG. 4 schematically illustrates the structures of the plasmids pB6A, pB6B; and pB6C.

The CBS 303.80 DNA fragment which was in the form of the vector B6 clone contained no cleavage sites for the restriction endonucleases BamHI, ClaI, EcoRI, HindIII, PstI, PvuII, SalI, KpnI, HpaI, SalI and XbaI. A unique HindII site in the cloned DNA fragment was converted into a BamHI site by integration of a BamHI linker (5'pCCGGA-TCCGG-3') into the plasmid B6 which had been partially cut with HindII (FIG. 3). One of the resulting plasmids (pB6A, FIG. 4) no longer resulted in expression of D-hydantoinase. Consequently, the integration of the BamHI linker must have taken place in the region of the gene. For this reason, sequencing was carried out in both directions from the BamHI cleavage site after 5'-$^{32}$p labeling (XXIV). Kinase treatment was followed by secondary cleavage with EcoRI, and the two fragments which were to be sequenced were purified on low-melting agarose. The position and the orientation of the D-hydantoinase gene resulted from the sequence data obtained. The stop codon is located after 225 nucleotides downstream of the BamHI site. It was possible accurately to assign the reading frame because the sequenced fragment correlated exactly with a sequenced tryptic fragment over 10 amino acid residues (NNDYNGFEGF; see Example 1.3i). Specific sequencing of the D-hydantoinase gene was carried out with the aid of overlapping deletion mutants (XXV).

(i) Kinase treatment of the linkers

The BamHI linker (5'-CCGGATCCGG-3') and HindIII linker (5'-GCAAGCTTGC-3') were converted into the 5'-phosphorylated forms in a 20 μl reaction mixture in an amount of 250 pmol in 60 mM tris-HCl, pH 7.5, 10 mM MgCl$_2$, 15 mM DTT, 1 mM spermine, 100 μM ATO, 8 U of T4 polynucleotide kinase (PL Biochemicals) at 37° C. for 30 min. The mixtures were then frozen and aliquots were used directly for ligation (see below).

(ii) Integration of the BamHI linker into plasmid B6 which has been partially cleaved with HindII 4 μg of plasmid B6 which had been isolated in a known manner was digested with 1 U of HindII (Boehringer, Mannheim) at 37° C. for 10 min. Phenol extraction and concentration by ethanol precipitation were followed by integration of the BamHI linker in a 50 μl mixture with approximately a 50-fold excess of the linker based on the free ends of the plasmid (100 pmol of linker, 2 pmol of ends ≐4 μg of B6 partially cleaved with HindII, 66 mM tris-HCl, pH 7.5, 6.6 mM MgCl$_2$, 10 mM DTT, 0.4 mM ATP, 5 U of T4 DNA ligase; 15° C., 14 h). Phenol extraction and ethanol precipitation were followed by complete digestion of the ligated DNA in 40 μl using 10 U of BamHI. The reaction mixture was fractionated on a 1% agarose gel (Low-melting agarose, Biorad). Linear plasmid was eluted by phenol extraction of the molten gel segment and was purified on DE52 (Whatman; binding in 0.15M NaCl, 10 mM tris-HCl, pH 7.5, 1 mM EDTA, elution with 1M NaCl, 10 mM tris-HCl, pH 7.5, 1 mM EDTA) and concentrated by ethanol precipitation. The yield was about 1 μg. 100 ng of DNA were cyclized in a 20 μl ligation mixture (66 mM tris-HCl, pH 7.5, 6.6 mM MgCl$_2$, 10 mM DTT, 0.4 mM ATP; 15° C., 14 h) using 0.5 U of T4 DNA ligase, and were transfected into *E. coli* HB 101 cells treated with CaCl$_2$. Recombinant clones were selected in a known manner. The possible recombinant plasmids pB6A, pB6B, pB6C (FIG. 4) were assigned by double digestion with EcoRI/BamHI. The plasmid pB6A was used for the sequencing (XXIV) which took place in both directions from the BamHI site (see FIG. 4). The plasmid pB6B was used as starting material for the generation of delts 5' and delts 3' mutants, which were prepared as follows.

(iii) B6 delta 5' mutants 7.5 μg of pB6B (FIG. 4), linearized with BamHI, were incubated with 2.4 U of Ba131 (BRL) in 100 μl of 12 mM CaCl$_2$, 12 mM MgCl$_2$, 600 mM NaCl, 20 mM tris-HCl, pH 8.0, and 1 mM EDTA at 25° C. 16 μl samples were taken after 4 and 6 min. The samples were immediately treated with phenol and combined. Two samples after 9 and 11 min and after 14 and 16 min were treated correspondingly. Chloroform extraction and concentration by ethanol precipitation were followed by cutting the DNA with Kornberg polymerase (PolI) so as to form blunt ends in order subsequently to attach a linker. The PolI treatment was carried out in 100 μl of 120 mM K-PO$_4$, pH 6.9, 6 mM MgCl$_2$, 1 mM dATP, 1 mM dTTP, 1 mM dGTP, 1 mM dCTP, 5 mM DTT, 1.5 μl of alpha-$^{32}$p-dATP, 400 Ci/mmol, 10 mCi/ml, and 10 U of DNA polymerase I (Boehringer, Mannheim) at 15° C. for 2 h with DNA which had been treated with 2 μg of Ba131. The reaction mixtures were then fractionated on Sephadex G50 (Pharmacia) in 100 mM NaCl, 50 mM tris-HCl, pH 7.5, 5 mM EDTA. The DNA in the exclusion volume was bound to DE52 (Whatman) in 0.15M NaCl, 10 mM tris-HCl, pH 7.5, 1 mM EDTA, eluted with 1M NaCl, 10 mM tris-HCl, pH 7.5, 1 mM EDTA, and precipitated with ethanol. The subsequent integration of a BamHI linker was carried out as described above in 30 μl. Extraction with phenol and chloroform and concentration by ethanol precipitation were followed by digestion of the samples with BamHI and fractionation and purification in a conventional manner on 0.8% low-melting agarose (gel concentration 0.8%).

The DNA which had thus been purified was religated in 20 μl mixtures using 0.5 U of T4 DNA ligase (12° C., 12 h). 10 μl of each ligation mixture were used to transfect *E. coli* HB101 cells which had been treated with CaCl$_2$, and the resulting recombinants were selected in a known manner. 15 plasmids were isolated and characterized from the Ba131 treatments for 4 to 6 min and from those for 9 to 11 min. The plasmids delts B6 5'A, -B, -E, -I and -K were sequenced from the BamHI cleavage site, in accordance with XXIV, as described above (secondary cleavage with EcoRI (see FIG. 5)).

(iv) B6 delts 3' mutants

The 3' mutants were generated in the same manner as the 5' mutants.

The DNA which was used to start was pB6B (see FIG. 4) after linearization with SmaI (FIG. 5). 10 μg were incubated in a reaction volume of 33 μl with 1.4 U of Ba131 in the buffer concentration indicated above. 3 μl samples were taken after 2 and 4, 6 and 8, 10 and 12, 14 and 16, and 18 and 20 min, treated with phenol, and worked up in pairs. PolI repair was followed by integration of the HindIII linker into the plasmid DNA, and the latter was digested with HindIII and religated under known conditions and then transfected into HB101 cells. After characterization of 48 recombinant plasmids (treatment with Ba131 for from 2 to 12 min) the 3' deletion mutants O, P, R and S were obtained. The position of the HindIII cleavage site was established by restriction mapping and sequencing. Sequencing was effected starting from the HindIII site with secondary cleavage using EcoRI in accordance with XXIV.

The sequence data obtained with the steps described under 1.7 ii-iv are compiled in FIG. 6. The coding region of the D-hydantoinase gene extends from nucleotide 327 to nucleotide 1435. The three nucleotides which signal the start of translation, and the translation stop signal, are indicated by boxes. Region 1 within the sequence corresponds to a length of 250 ±50 nucleotides, and region 3 corresponds to 90 ±1 nucleotides. Region 2 corresponds to a sequence NN or NNN. (N=A, G, C or T). The corresponding regions are indicated by boxes.

1.8 Optimization of expression

The recombinant plasmid delta B6 5'E still contains about 250 nucleotides of CBS 303.80 DNA upstream of the translation start codon of the D-hydantoinase gene after the SalI recognition site, which was formerly present in the plasmid pB6b, has been replaced by a BamHI cleavage site with deletion of the adjacent 200 to 300 nucleotides (see 1.7 iii).

Figure 5:
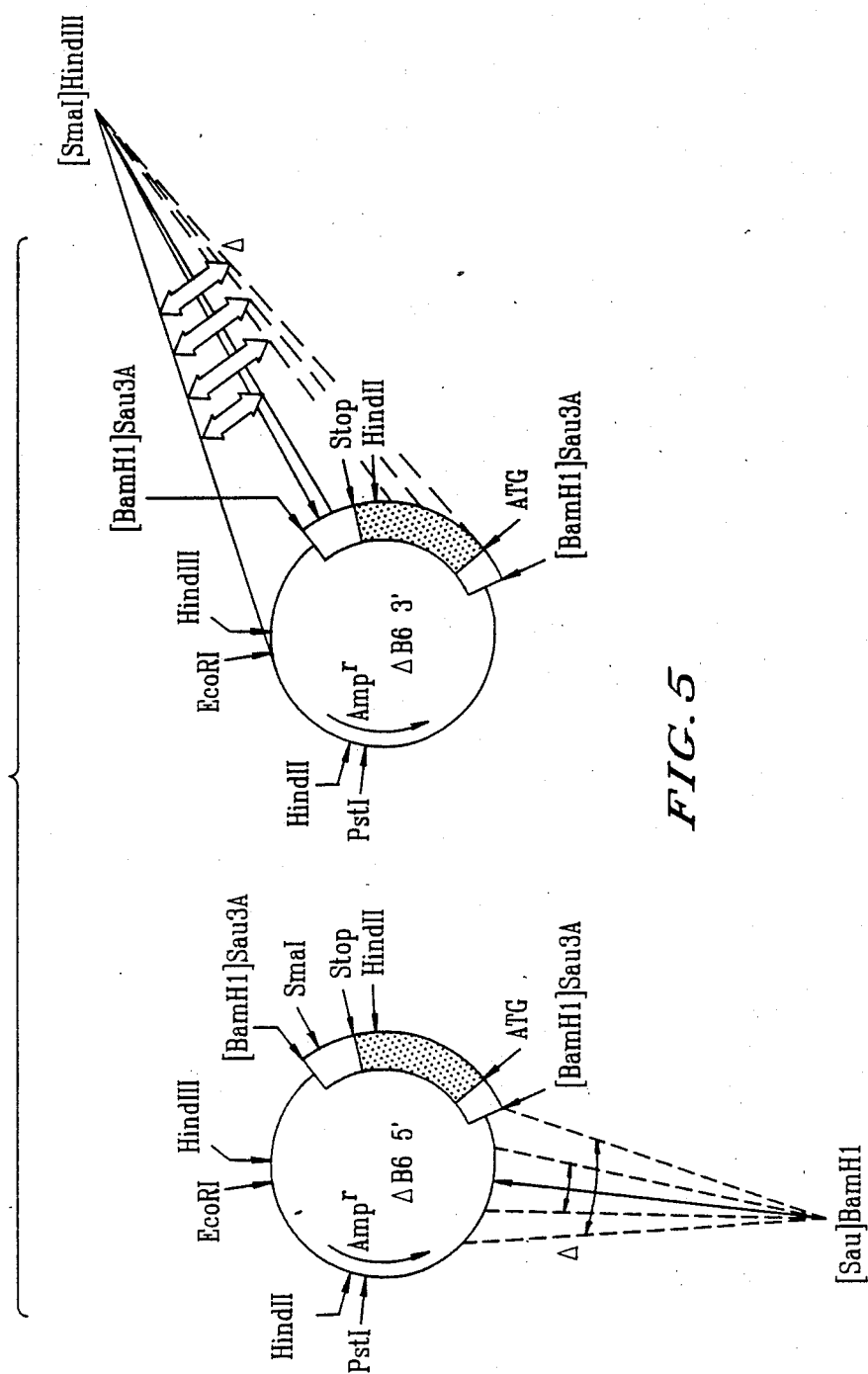
FIG. 5 schematically illustrates the structures of the plasmids ΔB6 5′ and ΔB6 3′.
Figure 7:
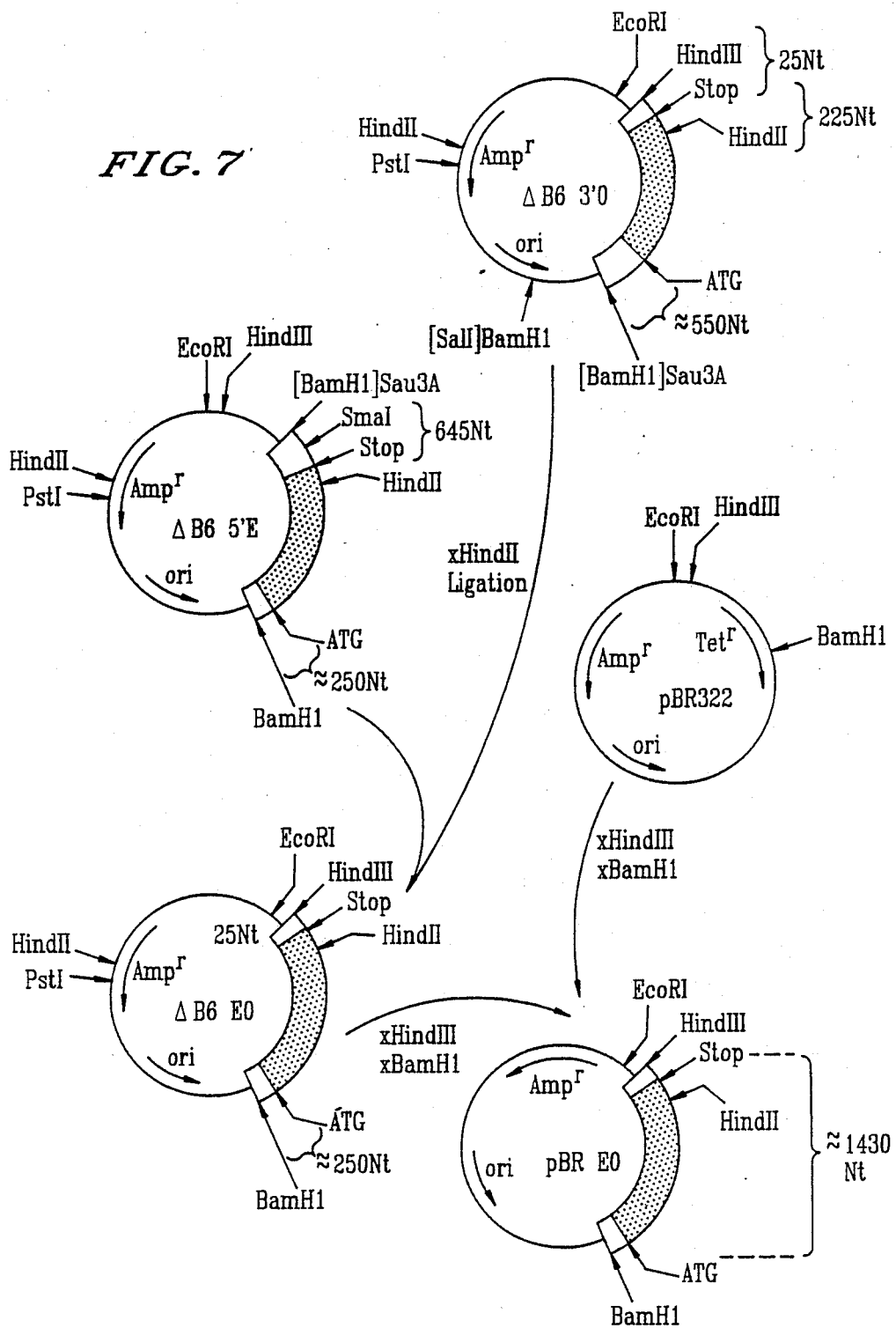
FIG. 7 illustrates a sequence of steps in a procedure for optimizing the expression of a hydantoinase gene.
Figure 8:
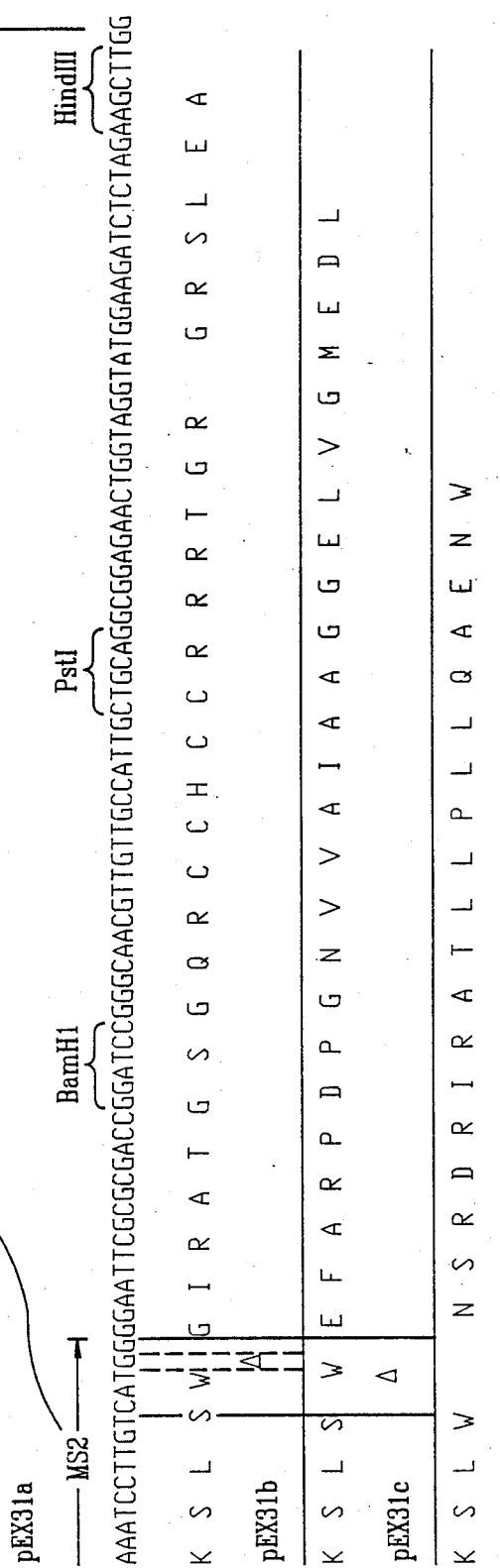
FIG. 8 schematically illustrates the structures of plasmids pEX31a-c.

*E. coli* HB 101 cells which have been transformed with this plasmid express enzymatically active D-hydantoinase. In the same way, starting from the SmaI cleavage site located in the 3'-flanking DNA sequence, the SmaI cleavage site was replaced by a HindIII cleavage site (FIG. 5 and 1.7 iv). This entailed the accompanying CBS 303.80 DNA sequence being eliminated apart from 25 nucleotides downstream of the translation stop codon of the D-hydantoinase gene (clone delts B6 3'0). The HindII fragment from the plasmid delts B6 3'0 was transferred into the plasmid delts B6 5'E to construct a new plasmid which still possesses about 250 nucleotides of foreign DNA upstream of the hydantoinase gene and 25 nucleotides of foreign DNA downstream of the stop codon of the gene (delts B6 EO, FIG. 7). Another deletion of the approximately 250 nucleotides of foreign DNA upstream of the hydantoinase gene proved impossible in the constructed plasmid delta B6 EO; this was possibly due to adverse effects of further bal deletions on the origin of replication of the vector (pBR327). In order to introduce further deletions the D-hydantoinase gene was cloned from delta B6 EO into pBR322 as the BamHI/HindIII fragment in a conventional manner. The resulting plasmid pBR EO (FIG. 7) was then linearized with BamHI and shortened with Bal31 as described above. After completion of the Bal31 digestion, repair of the ends with T4 DNA polymerase, and insertion of the BamHI linker and after transformation of E. coli HB101, 8 clones whose plasmid DNA exhibited, after BamHI/HindII digestion, a D-Hydantoinase gene fragment in the appropriate size range of 1.5 to 1.3 kb were selected. The D-hydantoinase gene was cut out of these plasmids, after isolation of the DNA in a conventional manner, by BamHI/HindIII digestion and was integrated into the plasmids pEX31a, b and c, the recipient plasmids previously also having been digested with BamHI and HindIII. The plasmids pEX31a–c are derived from the plasmid pPLC24 (XXVI) and contain the heat-inducible lambda promoter pl as well as, downstream of 97 amino acid codons of MS2 replicase, a polylinker region which allows coupling of a foreign gene onto the MS2 replicase gene in all three reading frames in constructs a–c (FIG. 8). The ligation products were transformed into E. coli strain N4830 (PL Biochemicals) which contains the gene for the thermolabile lambda repressor cI 857. Ampicillin-resistant transformants were obtained by incubation at 28° C. Clones which produced D-hydantoinase after heat induction were initially detected immunologically.

For this purpose, individual colonies were transferred into 150 µl of LB/Amp medium in the round-bottomed wells of microtiter plates, shaken at 28° C. overnight, transferred in 1:3 dilution into fresh medium (120 µl), and incubated in a microtiter plate, with shaking, at 42° C. for 3 h. After addition of 20 µl of 10% SDS solution the microtiter plate was covered with sealing film and incubated for 1 h on the surface of a water bath at 50° C. to complete lysis of the bacteria. The lysates were then transferred by suction, using a suitable device (Hybridot manifold 1050 MM supplied by BRL), onto a nitrocellulose sheet (BA85, Schleicher and Schuell) and, after washing with PBS buffer, were treated in a conventional manner (XXVII) with a 1:150 dilution of a D-hydantoinase antibody (IgG fraction of a rabbit antiserum) and then, after the first antibody had been washed out, with anti-rabbit IgG antibody coupled to horseradish peroxidase, with color detection of the bound horseradish peroxydase by means of o-dianisidine/$H_2O_2$. 8 of these clones showed enzymatic activity in converting methylthioethylhydantoin, irrespective of which reading frame of the plasmids pEX31a–c the D-hydantoinase gene fragments had been cloned into. The expression of enzyme activity was heatinducible. Clones IF10, 3A8 and IID2 showed the highest enzyme activities. They were a factor of 40 greater than that of the starting strain, based on moist biomass, on fermentation in the following medium: 5 g of yeast extract, 2.5 g of tryptone, 10 g of nutrient broth, 0.258 g of $Na_3PO_4 \times 12H_2O$, 10 ml of Castenholz basal medium per l. The cells were incubated at 30° C. until the $A_{600}$ was 0.3, heated at 45° C. for 15 min and fermented at 37° C. for 5 h. The cells were centrifuged, washed in solution A+1 mM $MnCl_2$ and were used in this buffer directly for the conversion of the hydantoins.

The junction between the vector sequences and the D-hydantoinase gene in the expression vectors IF10, 3A8 and which are derived from plasmids pEX31a, b and c and express CBS 303.80 D-hydantoinase was identified by sequencing. The junction is indicated in FIG. 6 by an arrow and the name of the corresponding construction each case. The junction is effected via a BamHI linker at the base of the arrow, the linker sequence not being shown in FIG. 6. 1.9 Characterization of the CBS 303.80 D-hydantoinase from recombinant E. coli clones For the molecular characterization of the D-hydantoinase from E. coli strains modified by gene manipulation, a 500 ml culture of HB101 was incubated with the plasmid B6 in LB/Amp at 37° C., shaking for 16 h, and working up was carried out as described under 1.5 to obtain enzymatically active D-hydantoinase, the amounts of buffer being increased by a factor of 10. After high-speed centrifugation of the clear lysate for 1 h at 4° C., the supernatant was adjusted to 0.1% in polymin P, heated at 70° C. for 2 min, and centrifuged at low speed for 15 min. The supernatant was concentrated 5-fold in an Amicon pressure cell. 30 µl of the concentrate were applied to an isoelectric focussing gel (pH 3.5–9.5; Ampholine PAGE plate LKB). Pure D-hydantoinase from CBS 303.80 was applied in parallel as a control. After the isoelectric focussing was complete, both lanes were cut into 3 mm segments. The gel segments were used directly for the assay for enzymatically active D-hydantoinase by conversion of methylthioethylhydantoin into N-carbamoylmethionine as described above. The D-hydantoinases from E. coli HB101 (B6) and CBS 303.80 had the same isoelectric point.

4 l of a culture of E. coli HB101 (B6) were worked up to produce a clear lysate as described above. After high-speed centrifugation at 4° C. for 60 min, the supernatant was adjusted to 0.4% in polymin P, heated at 70° C. for 2 min, and centrifuged at medium speed for 15 min. 165 ml of the supernatant were chromatographed on an affinity column which had been prepared by binding 1 ml of rabbit D-hydantoinase antiserum onto 1 g of Sepharose activated with cyanogen bromide (XXVIII). 5 µg of the eluted D-hydantoinase were fractionated on an ~ SDS gel (5% loading gel, pH 6.8, 10% running gel, pH 8.8) in tris-glycine buffer (XXIX). Authentic D-hydantoinase from CBS 303.80 was fractionated as a control. The protein bands were visualized by staining with Coomassie Brilliant Blue. D-Hydantoinase from E. coli and CBS 303.80 migrated at the same rate.

EXAMPLE 2

Shotgun cloning of the hydantoinase gene from Lu1220
2.0 Isolation of thermophilic Bacillaceae Thermophilic, aerobic, sporogenic bacteria having hydantoinase activity can be isolated from soil samples, plant material (especially compost) and water samples (preferentially nutrient-containing samples) by the following process (see also I):

A spatula-tip of the sample is suspended in nutrient solution or saline (0.85% NaCl). Water samples are examined as such, the sample volume being about 10 ml. The sample is pasteurized by heating at 80° C. for 10 min. Decimal dilutions of aliquots of the pasteurized samples are prepared in a conventional manner and streaked onto nutrient agar. The dishes containing nutrient agar are packed in plastic film and incubated at 60° C. for 1 to 4 days. The colonies which develop are removed and purified by re-peated transfers onto agar cultures. The resulting pure cultures are tested for hydantoinase activity.

A strain obtained in this way, which we have called Lu 1220, was used for the example.

2.1 Preparation of the DNA 200 ml of Castenholz medium were inoculated with a colony of Lu 1220 which was cultivated, agitating (160 rpm) at 60° C., to 190 Klett units. After centrifugation at 4,000 rpm and 4° C. for 20 min (Heraeus Minifuge) the wet weight was found to be 1.16 g. The residue from centrifugation was washed with 25 ml of 150 mM NaCl, 100 mM EDTA, pH 8.0, and pelleted once more. After the cells had been taken up in 15 ml of 150 mM NaCl, 100 mM EDTA, pH 8.0 and 0.5 ml of lysozyme had been added (Sigma; 10 mg/ml in 150 mM NaCl, 100 mM EDTA, pH 8.0) the cells were incubated at 37° C. for 60 min, and then 1 ml of 25% aqueous SDS solution was added, and the mixture was incubated at 60° C. for 10 min (cell lysis). 0.25 vol. of 5M $NaClO_4$ was added at 20° C. Subsequent working up was as described in Examples 1.1 to 1.2. The DNA was finally taken up in 150 $\mu$l of 20 mM tris-HCl, pH 8.0. The final purification was effected by CsCl gradient centrifugation. 75 $\mu$l of DNA solution was introduced onto a CsCl solution (7 ml of $H_2O$, 0.11 ml of 100 mM $Na_2B_4O_7$, 1.36 g of CsCl (n=1.400)), centrifuged at high speed in a TST 41 rotor (Kontron ultracentrifuge) at 20° C. for 30 h, and the DNA was selected from 2 of 15 0.5 ml fractions. The DNA was precipitated by addition of 3 ml of $H_2O$ and 12 ml of ethanol at 0° C., washed 2 × with 80% ethanol, and dissolved in 100 $\mu$l of 20 mM tris-HCl, pH 8.0. The yield was 120 $\mu$g of DNA.

2.2 Cosmid shotgun cloning

Lu1220 DNA was partially cut with Sau3A (20 $\mu$g of DNA with 1 or 3 U of Sau3A at 37° C. for 1 h). It was ascertained by electrophoresis in 0.8% agarose gels that the mean fragment size was >20 kb. The fragments were, as described in Example 1, ligated into the BamHI recognition site of pHC79, packaged in vitro, and converted into a cosmid gene bank via E. coli HB101. Duplicates of 1,600 individual colonies were transferred into 100 $\mu$l of LB/Amp (cultures on microtiter plates). One plate of each was stored as a glycerol culture (20% glycerol) at −70° C.

2.3 Identification of the cosmid clones positive for Lu1220 D-hydantoinase using an immunoassay.

A polyclonal antibody was available (obtained as described in Example 1 for polyclonal antibodies against CBS 303.80), for the D-hydantoinase from Lu1220 using which it was possible to carry out colony-specific detection, as described in Example 1, of the D-hydantoinase produced in E. coli by its own promoter activity. For this purpose, 1,500 clones were tested, as described in Example 1 and in accordance with XVIII, for the expression of Lu1220 D-hydantoinase sequences. 8 colonies proved to be anti-D-hydantoinase Lu1220 IgG antigen positive. All the clones were assayed for enzymatic activity (150 ml cultures in LB/Amp, 1 mM $MnCl_2$). The cultures were cultivated at 37° C. to ~ 300 Klett units, the cells were centrifuged at medium speed and 4° C. for 20 min (Minifuge, Heraeus) and the pellet was washed with 15 ml of solution A (50 mM tris-HCl, pH 8.0, 10% sucrose), 1 mM $MnCl_2$, resuspended in 1.3 ml of solution A, 1 mM $MnCl_2$ and, after addition of 270 $\mu$l of lysozyme (10 mg/ml) in solution A, the mixture was incubated at 20° C. for 20 min. 330 $\mu$l of 0.25M EDTA, pH 8.0, were added and, after incubation at 20° C. for 5 min, 1.67 ml of solution B were immediately mixed in and the mixture was centrifuged at high speed at 4° C. for 1 h. 0.5 ml of borax buffer, pH 8.15, 0.13 ml of 1M $MgCl_2$ and 0.5 ml of 5% methylthioethylhydantoin were added to each 2 ml of supernatant, which was shaken at 60° C. for 4 h. 1.5 ml of each of these mixtures were centrifuged in an Eppendorf bench centrifuge for 5 min. 1.2 ml of the supernatant were mixed with 0.168 ml of phosphoric acid diluted 1:10, filtered sterile and analyzed by HPLC. One culture (C5, see FIG. 9) proved to be a producer of enzymatically active D-hydrantoinase.

2.4 Plasmid subcloning in pBR327

Plasmid DNA was prepared from a 100 ml culture of C5 in LB/Amp (see Example 1). 10 $\mu$g of C5 DNA were cleaved with 1.5 U of Sau3A in 100 $\mu$l at 37° C. for 1 h, and the mixture was directly applied to 0.8% low-melting agarose (Biorad). The DNAs with a size of from 1,500 to 3,000 nucleotides were eluted from the gel, precipitated and dissolved in 20 $\mu$l of 20 mM tris-HCl, pH 8.0, 0.1 mM EDTA. 8 $\mu$l (200 ng) of C5 DNA which had been partially cleaved with Sau3A were ligated with an equimolecular amount of pBR327 in 25 $\mu$l (1 U of T4 DNA ligase, NEN. 15° C. overnight). The pBR327 vector was cleaved with BamHI and 5'-dephosphorylated with calf intestine phosphatase (Boehringer Mannheim) in order to suppress self-ligation of the vector (XXX).

10 $\mu$l of the ligation mixture were transformed into E. coli HB101 (XXXI), and the transformation mixtures were plated onto LB/Amp plates. The result was 500 colonies which were, as described for the cosmid clones, transferred into microtiter plates and in turn tested for D-hydantoinase antigen in accordance with XVIII. 4 clones indicated production of antigen. Plasmid DNA was prepared from 100 ml LB/Amp cultures of these 4 representatives, and 50 ml samples were used as described above for enzyme assays for D-hydantoinase. 2 clones exhibited enzymatic activity. The plasmids from these clones (F2 and B4) were evidently identical and had integrated unexpectedly large DNA fragments (~ 8 kb), whereas two others contained integrated fragments 1.9 kb and ~2.1 kb in length respectively.

Figure 9:
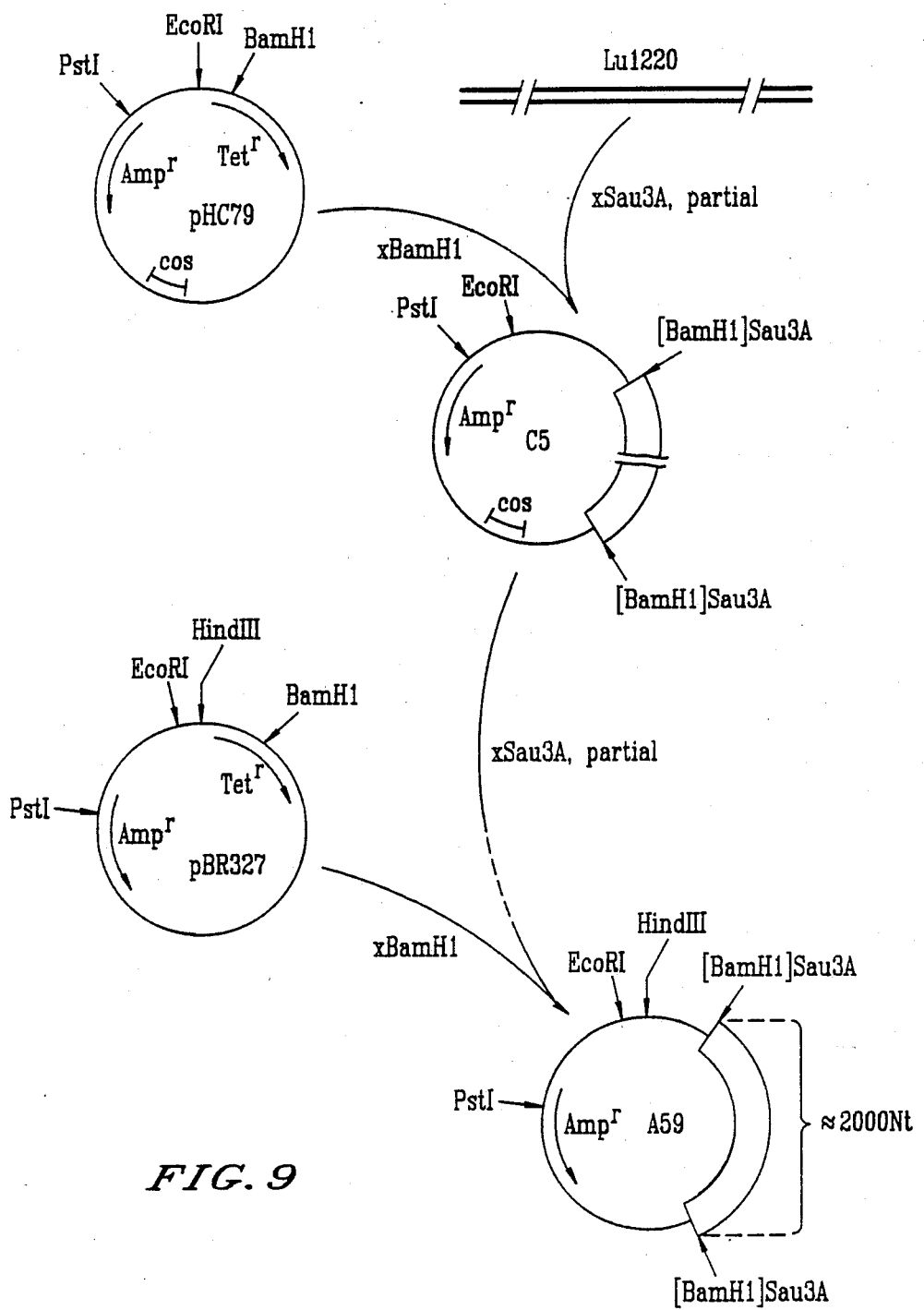
FIG. 9 illustrates a sequence of steps for preparing plasmid A59.

Plasmid DNA from clone F2 was used for further subcloning to obtain a clone with an insert of the shortest possible length but nevertheless producing enzymatically active D-hydantoinase:

10 $\mu$g of F2 DNA were digested with 3 U of Sau3A in 100 $\mu$l for 1 h, and fractionation by size (1,500 to 3,000 bp) was carried out on 0.8% low-melting agarose as described above. The fragments were integrated into the BamHI site of pBR327 and transformed into HB101 as described. 650 colonies were obtained, of which 23 colonies reacted antigen-positive in the Broome-Gilbert assay (XVIII), and 4 of these showed very strong signals, while 8 colonies proved to be producers of active D-hydantoinase (e.g. A59 and E64). The clone A59 proved to have the highest productivity and had an insert 1,734 bp in length (FIG. 9).

Figure 10:
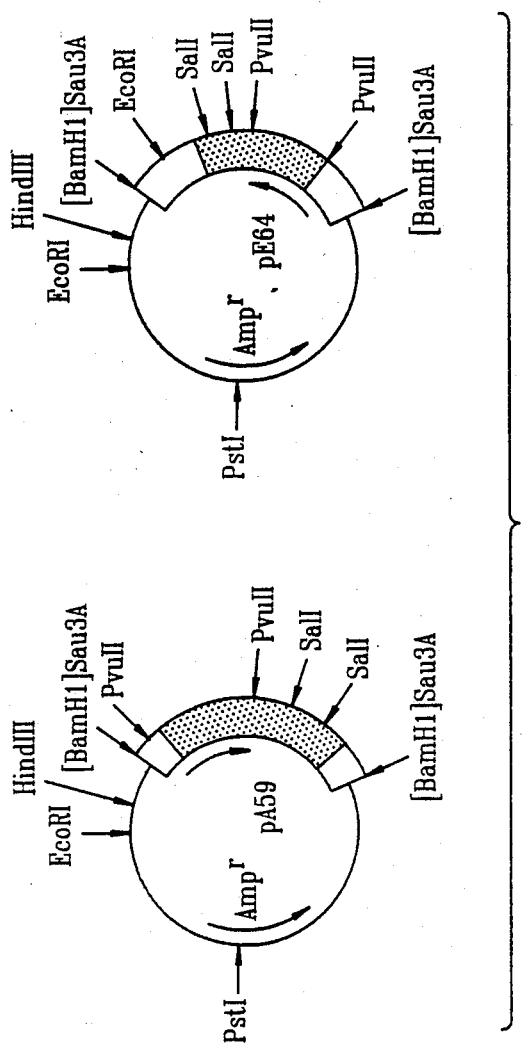
FIG. 10 schematically illustrates the structures of the plasmids pA59 and pE64.

A59 was used for optimization of expression, and A59 and E64 (FIG. 10) were used for sequence analysis of the D-hydantoinase gene.

2.5 Sequencing

Figure 11:
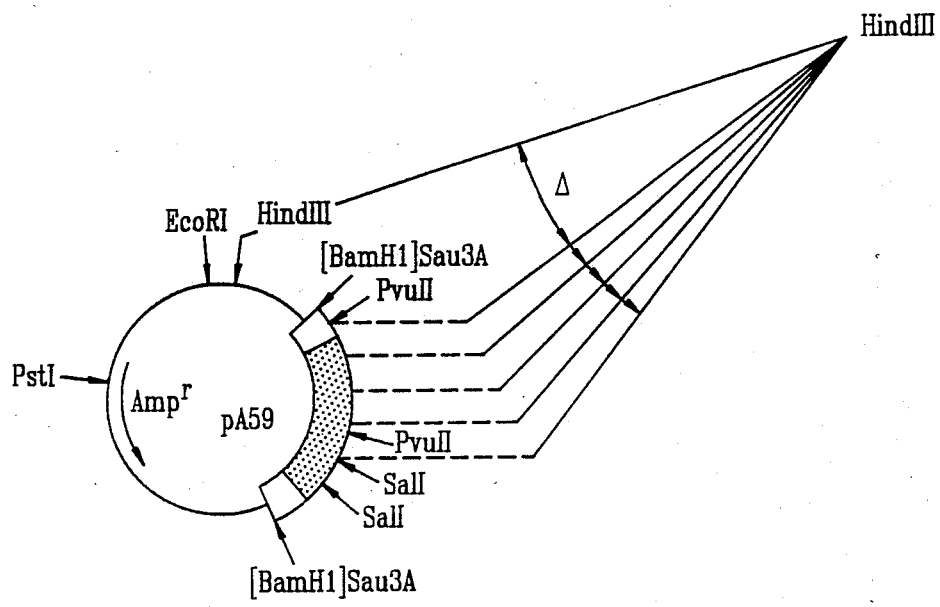
FIG. 11 further schematically illustrates the structure of the plasmid pA59.

The sequencing was carried out using the strategy depicted in FIG. 11. Use was made not only of the natural restriction sites for the sequencing but also of artificial restriction sites which had been introduced into the plasmids A59 and E64 by the method of Frischauf et al. (XXV). The aim was to obtain a series of one-sided deletion mutants bounded by linker cleavage sites (delta 5') so that the sequencing of the fragments results in a complete, overlapping sequence of the insert (FIG. 11. The arrow on the hydantoinase gene indicates the direction of reading, and the black section of the insert indicates the coding region). The sequencing was carried out in accordance with XXIV.

40 μg of plasmid A59 DNA were digested with 200 pg of DNase (Worthington, stock solution: 1 mg of DNase in 1 ml of 50% glycerol, 150 mM Na acetate, pH 5.0, 1M NaCl, 0.5 mg/ml gelatin) in 250 μl of DNase I buffer (20 mM tris-HCl, pH 7.5, 1.5 mM $MnCl_2$, 100 μg/ml gelatin) at 24° C. for 6 min, the reaction was stopped with 5 μl of 0.5 M EDTA, pH 8.0, and the mixture was extracted by shaking with 250 μl of phenol (equilibrated with buffer), treated with chloroform, extracted with ether, and fractionated by electrophoresis on a 0.8% low-melting agarose gel (100 V/20 cm, 2 h). The band of the linearized plasmid was cut out, and the DNA was eluted, purified on DE52 cellulose (Whatman) and dissolved in 20 μl of 20 mM tris-HCl, pH 7.5, 0.1 mM EDTA (~5 μg of DNA). The ends of the DNA were made flush with 5 U of polymerase I Klenow fragment (Boehringer Mannheim) by incubation at 20° C. for 30 min (XXXII). Thereafter, a 50-fold molar excess of kinase-treated HindIII linkers (5'-GCAAGCTTGC-3'; P&L) was ligated onto 1.5 μg of linearized A59 DNA (~0.8 pmol of ends) in a 25 μl ligation mixture (XXII) in the presence of 10 U of T4 DNA ligase (NEN). Incubation at 15° C. overnight was followed by inactivation of the ligase at 65° C. for 10 min. 25 μl of Y100 buffer (100 mM NaCl, 10 mM tris-HCl, pH 7.5, 6 mM $MgCl_2$, 1 mg/ml gelatin, 6 mM β MSH) were added, and the DNA was digested with 5 U of HindIII (Boehringer, Mannheim) at 37° C. for 1 h. Fractionation of the resulting DNA fragments on a 0.8% low-melting agarose gel resulted in a smeared track of DNA fragments whose upper limit coincided with the length of the plasmid A59. All the DNase I cleavage sites outside the HindIII cleavage site on pBR327 result in a pair of smaller plasmid fragments. The track on the gel was cut with a razor blade into small segments so that a series of fragment fractions selected according to length could be religated separately.

The fractions were religated as described by Frischauf et al. (XXV), in the presence of the low-melting agarose, and were transformed into E. coli HB101 (13 mixtures). A mean of 50 transformants was obtained for each fraction, and 2 of each of these were analyzed via their plasmids. The DNA sequences obtained from the overlapping deletion plasmids provided the total sequence shown in FIG. 12 for the Lu1220 D-hydantoinase gene and the marginal sequences which were also determined.

The coding region of the D-hydantoinase gene from Lu1220 extends from nucleotide 391 to nucleotide 1746.

The three nucleotides which signal the start of translation, and the translation stop signal, are shown by shading.

2.6 Construction of E. coli strains expressing Lu1220 D-hydantoinase and having increased productivity The fractions of the A59 delta 5' deletion mutants which had been prepared for the sequencing were used as starting plasmids to generate a large pool of further deletion mutants with a boundary close to the ATG start codon. This entailed starting from the fraction of deletion mutants whose HindIII linkers were located in the vicinity of the PvuII cleavage site 52 nucleotides upstream of the start codon (test for the presence of the cleavage site). The colonies which belonged to this fraction were combined and used together for a plasmid preparation. The DNA (10 μg) was linearized with HindIII and briefly treated with 2.4 U of Bal31 in 100 μl (XXXIII) at 25° C. for 30 sec. The reaction was stopped by addition of phenol, and the DNA was worked up. The DNA was incubated with DNA polymerase I at 15° C. in a 100 μl reaction mixture for 2 h (XXXIV) in order to obtain flush ends on the DNA.

This was followed by addition of BamHi linker (5'-CCGGATCCGG-3', P&L) (1.5 μg of DNA, ~1 pmol of ends, 84 pmol of linker, 20 U of T4 DNA ligase, NEN) in 25 μl at 15° C. overnight. The ligase was then inactivated at 65° C. for 10 min, and the DNA was digested with BamHI. The DNA was purified in 0.8% low-melting agarose as a diffuse band, and was isolated and then ligated in 100 μl and transfected into E. coli HB101. The resultant colonies totaled 1,822. The DNA of 96 colonies at random was examined and mapped by BamHi×PvuII restriction. 14 plasmids contained a PvuII/BamHI fragment (~925 bp), and hence a BamHI linker in the immediate neighborhood of the ATG start codon, and were sequenced starting from the BamHI linker. Only the A+G and C+T reactions were carried out because the exact sequence of the region was available. The plasmids p70, p62 and p51 had been digested with Bal31 as far as the positions indicated in FIG. 12. The junction between the vector sequences and the Lu1220 gene fragment for each is shown in FIG. 12 with an arrow and the name of the corresponding construct. The junction is effected via a BamHi linker at the base of the arrow; the linker sequence is not shown in FIG. 12. Since there is uncertainty about the sequence of the first 2 nucleotides, all three possible reading frames were taken into account on transformation of these plasmids into expression vectors.

Two systems were available as expression vectors: pEX31a-c and pCL547 (XXXVI). The vectors pEX31a-c were made available by Prof. Dr. H. Schaller of the University of Heidelberg, and the plasmid pCL547 was made available by Dr. K. Stanley, EMBL, Heidelberg.

The plasmids pEX31a-c are derived from pBR322 and contain the phage lambda pL promoter region which is coupled to the MS2 polymerase region (XXVI). The DNA sequence following 97 amino acid codons of the polymerase gene was linked via an EcoRI cleavage site in three continuous reading frames to a polylinker region. The D-hydantoinase gene sequences of plasmids p51, p62 and p70 were ligated into the BamHi cleavage site. For this purpose, the promoter-containing PstI-BamHi fragments of pEX31a, b and c (FIG. 8) were replaced by the corresponding fragment of p51, p62 and p70. The fragments were initially fractionated by electrophoresis in 0.8% of low-melting agarose, and eluted and precipitated, and then ligated in the presence of 7% polyethylene glycol (XXXV) and transfected into E. coli N4830.

32 of each of the resulting clones (pEX51a,b,c, pEX6-2a,b,c and pEX70a,b,c; ≈ 150 clones/mixture) were deposited for each reading frame in microtiter plates. The cultures (each in 100 μl of LB/Amp medium) were shaken at 28° C. overnight. At this temperature, the temperature-sensitive lambda repressor cI857, which is coded in the chromosomes of E. coli N4830, ensures effective repression of hydantoinase. Subsequently, to induce enzyme production, 10 μl of each were transferred into a fresh microtiter plate and shaken in 100 μl of LB/Amp medium at 28° C. for 5 h. The culture was then heated in a water bath at 42° C. for 15 min and shaken in an incubator at 42° C. for a further 3 h. The E. coli bacteria were subsequently each lyzed with 20 μl of 10% SDS and tested for the presence of Lu1220 D-hydantoinase antigen as described in Example 1.

Figure 13:
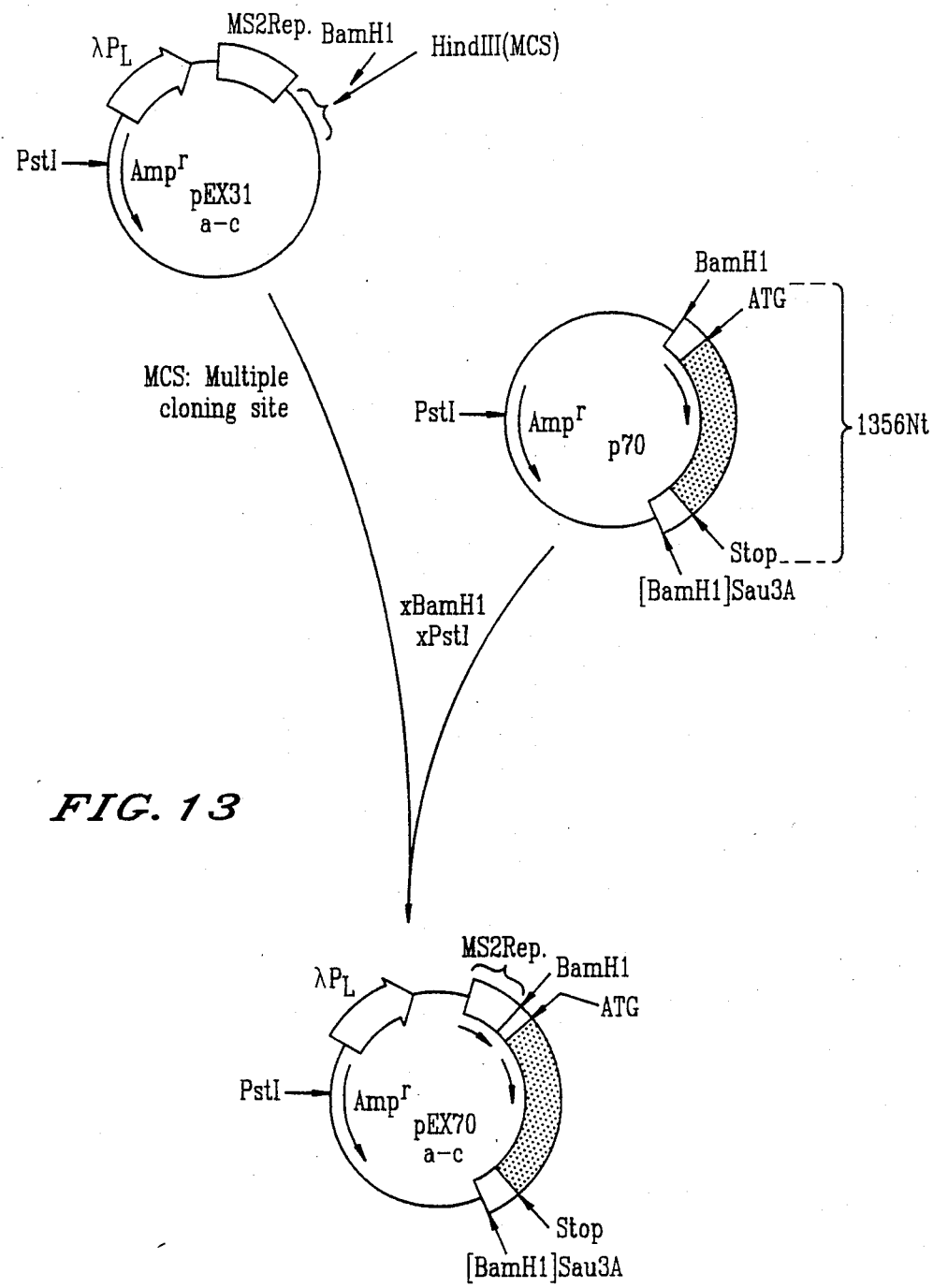
FIG. 13 illustrates a sequence of steps for the preparation of plasmid pEX70.

The result of the immunological test for expression of Lu1220 D-hydantoinase antigen was positive in reading frame b and negative with a and c in the case of plasmids pEX51 and pEX62; in the case of plasmids pEX70 all the reading frames were positive. 4 representatives of each of the antigen-positive microtiter cultures pEX62b, pEX51b and pEX70a,b and c were examined in 100 ml cultures for D-hydantoinase enzymatic activity. Only pEX62b, pEX70a, pEX70b and pEX70c proved to be active. The construct pEX70 is depicted in FIG. 13.

Figure 14:
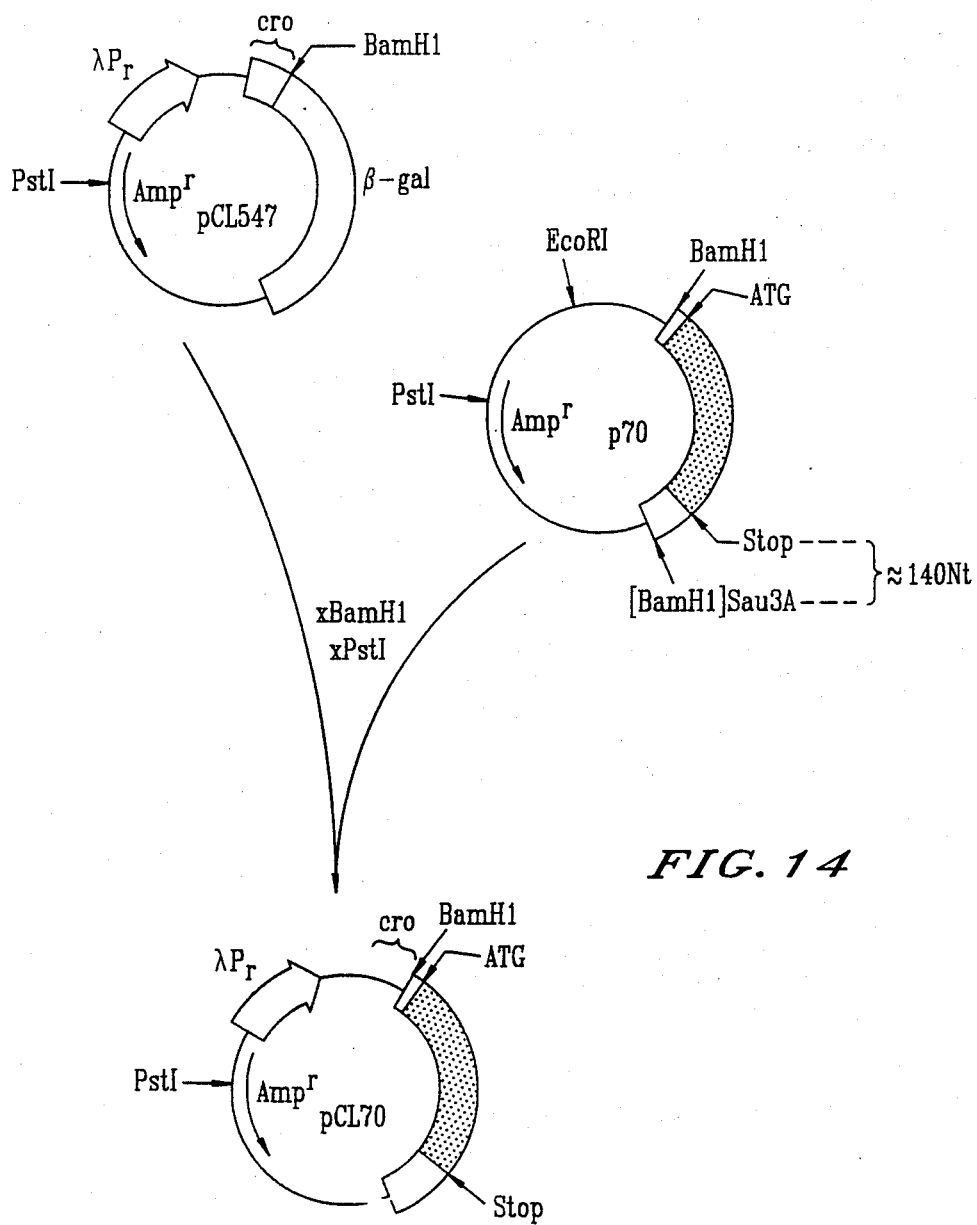
FIG. 14 illustrates a sequence of steps for the preparation of plasmid pCL70.

In the case of expression vector pCL547 (XXXVI), only one reading frame for D-hydantoinase gene integration was available. The BamHI/PstI fragments which contained the D-hydantoinase gene from p70 and p62 and p51 were integrated as described above between the unit BamHI cleavage site between the cro and β-galactosidase genes and the PstI cleavage site of the pBR portion (FIG. 14). Transformation into E. coli N 4830 was followed by testing of 4 colonies in each case for expression of enzymatically active D-hydantoinase Since the D-hydantoinase gene in these constructs is under the control of the lambda pr promoter/cI857 repressor, the synthesis of D-hydantoinase after heat-induction was measured as described above. Only the pCL70 constructs proved to be enzymatically active. Their resultant enzyme activity, based on moist biomass, in fermentation mixtures (see Example 1.5) after heat induction was 4 times that of the starting strain Lu1220.

Summary of the literature quoted:

I: German Laid-Open Application DOS 3,031,151
II: U.S. Pat. No. 4,237,224
III: European Laid-Open application EOS 41,313
IV: German Laid-Open application DOS 3,138,096
V: German Laid-Open application DOS 3,238,554
VI: J. Biochem. Tokyo 89 (1981), 667
VII: J. Mol. Biol. 77 (1973), 1
VIII: J. Biol. Chem. 242 (1968), 4409
IX: Gene 2 (1977), 95
X: Gene 9 (1980), 287
XI: Gene 11 (1980), 291
XII: Biotechnology Made Simple, A. Glossary of Recombinant DNA and Hybridoma Technology, PJB Publications, 18–20 Hill Rise, Richmond, Surrey, TW 106 UA, UK, 1983
XIII: Nature 215 (1967), 1285
XIV: Methods Enzym. 68 (1979), 281, 299
XV: J. Mol. Biol. 41 (1969), 459
XVI: Methods Enzym. 27 (1973), 942
XVII: J. Biol. Chem. 243 (1968), 3557
XVIII: Proc. Nat. Acad. Sci. 75 (1978), 2746
XIX: The Bacteriophage Lambda, Hershey, A.D., ed. Cold Spring Harbor, New York 1971, pages 259, 628, 226 et seq., 565–588
XX: Molecular Cloning, A Laboratory Manual, Cold Spring Harbour Laboratory, 1982, p. 86 et seq.
XXI: as XX, p. 133
XXII: as XX, pp. 146, 245 et seq., 286 et seq.
XXIII: Gene 6 (1979), 23
XXIV: Methods Enzym. 65 (1980), 499
XXV: Nucl. Acids Res. 8 (1980), 5541
XXVI: Gene 15 (1981), 81
XXVII: Nucl. Acids Res. 11 (1983), 4077
XXVIII: Affinity Chromatography, Principles and Methods, Pharmacia Fine Chemicals, June 1979, pp. 12 et seq., 92 et seq.
XXIX: Nature 227 (1970), 680
XXX: as XX, pp. 133, 297
XXXI: as XX, p. 249 et seq.
XXXII: as XX, p. 113 et seq., 394
XXXIII: as XX, p. 135 et seq.
XXXIV: as XX, p. 108, 113 et seq.
XXXV: Nucl. Acids Res. 11 (1983), 7853
XXXVI: EMBO J. 1 (1982), 1217

We claim:

1. The isolated DNA sequence coding for D-hydantoinase as shown in FIG. 6.

2. The isolated DNA sequence coding for D-hydantoinase as shown in FIG. 12.

3. A process for the preparation of mesophilic microorganisms which contain a hydantoinase which is active at elevated temperatures, which process comprises
   (i) isolating and digesting or shearing the DNA from a thermophilic microorganism which cleaves D-hydantoin;
   (ii) ligating the resulting DNA fragments with a cloning vector, to obtain a recombinant cloning vector;
   (iii) introducing said recombinant cloning vector into a mesophilic microorganism; and
   (iv) selecting those microorganisms which express enzymatically active hydantoinase, wherein said thermophilic microorganism is one member selected from the group consisting of CBS 303.80 and Lu1220 and said mesophilic microorganism is E. coli.

4. A mesophilic microorganism obtained by a process, comprising the steps:
   (i) isolating and digesting or shearing the DNA from a thermophilic microorganism which cleaves D-hydantoin;
   (iii) ligating the resulting DNA fragments with a cloning vector, to obtain a recombinant cloning vector;
   (iii) introducing said recombinant cloning vector into a mesophilic microorganism; and
   (iv) selecting those microorganism which express enzymatically active hydantoinase, wherein said thermophilic microorganism is one member selected from the group consisting of CBS 303.80 and Lu1220 and said mesophilic microorganism is E. coli.

5. An isolated DNA sequence coding for D-hydantoinase from a thermophilic microorganism selected from the group consisting of CBS 303.80 and Lu1220.

* * * * *